(12) United States Patent
Pudil et al.

(10) Patent No.: US 10,004,839 B2
(45) Date of Patent: Jun. 26, 2018

(54) MULTI-USE SORBENT CARTRIDGE

(71) Applicant: Medtronic, Inc., Minneapolis, MN (US)

(72) Inventors: Bryant J. Pudil, Plymouth, MN (US); Christopher M. Hobot, Tonka Bay, MN (US)

(73) Assignee: Medtronic, Inc., Minneapolis, MN (US)

( * ) Notice: Subject to any disclaimer, the term of this patent is extended or adjusted under 35 U.S.C. 154(b) by 334 days.

(21) Appl. No.: 14/722,094

(22) Filed: May 26, 2015

(65) Prior Publication Data

US 2015/0250937 A1    Sep. 10, 2015

Related U.S. Application Data

(63) Continuation-in-part of application No. 14/261,651, filed on Apr. 25, 2014.

(60) Provisional application No. 61/941,672, filed on Feb. 19, 2014, provisional application No. 61/909,372, filed on Nov. 26, 2013.

(51) Int. Cl.
   *B01D 35/00*    (2006.01)
   *A61M 1/16*    (2006.01)
   *B01J 20/02*    (2006.01)
   *A61M 1/14*    (2006.01)

(52) U.S. Cl.
   CPC ........ *A61M 1/1696* (2013.01); *B01J 20/0292* (2013.01); *A61M 1/14* (2013.01)

(58) Field of Classification Search
   None
   See application file for complete search history.

(56) References Cited

U.S. PATENT DOCUMENTS

| | | | |
|---|---|---|---|
| 1,617,288 A | 2/1927 | Kenney |
| 3,608,729 A | 9/1971 | Haselden |
| 3,617,558 A | 11/1971 | Jones |
| 3,669,880 A | 6/1972 | Marantz |
| 3,776,819 A | 12/1973 | Williams |
| 3,850,835 A | 11/1974 | Marantz |

(Continued)

FOREIGN PATENT DOCUMENTS

| | | |
|---|---|---|
| CN | 104936633 | 9/2015 |
| EP | 711182 B1 | 6/2003 |

(Continued)

OTHER PUBLICATIONS

Office Action for Chinese Application No. 2015/80009562.5 dated Jul. 3, 2017.

(Continued)

*Primary Examiner* — Richard C Gurtowski
(74) *Attorney, Agent, or Firm* — Kenneth Collier; Roger Hahn

(57) ABSTRACT

A sorbent cartridge comprising one or more detachable modules. The sorbent cartridge can have one or more modules contained therein having connectors connecting each of the modules. One or more of the modules can be reusable and the sorbent materials therein recharged. The sorbent cartridge can include a module containing an anion exchange resin, such as zirconium oxide, downstream of zirconium phosphate in the sorbent cartridge to recapture phosphate anions that leach out of the zirconium phosphate.

23 Claims, 13 Drawing Sheets

(56) References Cited

U.S. PATENT DOCUMENTS

| | | | |
|---|---|---|---|
| 3,884,808 A | 5/1975 | Scott | |
| 3,902,490 A | 9/1975 | Jacobsen et al. | |
| 3,989,622 A | 11/1976 | Marantz | |
| 4,073,725 A | 2/1978 | Takeuchi | |
| 4,094,775 A | 6/1978 | Mueller | |
| 4,206,054 A | 6/1980 | Moore | |
| 4,209,392 A | 6/1980 | Wallace | |
| 4,376,707 A | 3/1983 | Lehmann | |
| 4,460,555 A | 7/1984 | Thompson | |
| 4,581,141 A | 4/1986 | Ash | |
| 4,650,587 A | 3/1987 | Polak | |
| 4,661,246 A * | 4/1987 | Ash | A61M 1/1696 210/110 |
| 4,684,460 A | 8/1987 | Issautier | |
| 5,230,702 A | 7/1993 | Lindsay et al. | |
| 5,284,470 A | 2/1994 | Beltz | |
| 5,302,288 A | 4/1994 | Meidl | |
| 5,308,315 A | 5/1994 | Khuri | |
| 5,507,723 A | 4/1996 | Keshaviah | |
| 5,662,806 A | 9/1997 | Keshaviah et al. | |
| 5,770,086 A | 6/1998 | Indriksons | |
| 5,849,179 A | 12/1998 | Emerson et al. | |
| 5,858,186 A | 1/1999 | Glass | |
| 5,944,684 A | 8/1999 | Roberts | |
| 6,036,858 A | 3/2000 | Carlsson | |
| 6,114,176 A | 9/2000 | Edgson et al. | |
| 6,126,831 A | 10/2000 | Goldau et al. | |
| 6,521,184 B1 | 2/2003 | Edgson et al. | |
| 6,572,769 B2 | 6/2003 | Rajan | |
| 6,579,460 B1 | 6/2003 | Willis | |
| 6,627,164 B1 | 9/2003 | Wong | |
| 6,666,840 B1 | 12/2003 | Falkvall et al. | |
| 6,719,745 B1 | 4/2004 | Taylor | |
| 6,814,724 B2 | 11/2004 | Taylor | |
| 6,818,196 B2 | 11/2004 | Wong | |
| 6,861,266 B1 | 3/2005 | Sternby | |
| 6,878,283 B2 | 4/2005 | Thompson | |
| 6,878,285 B2 | 4/2005 | Hughes | |
| 6,960,179 B2 | 11/2005 | Gura | |
| 7,033,498 B2 | 4/2006 | Wong | |
| 7,101,519 B2 | 9/2006 | Wong | |
| 7,208,092 B2 | 4/2007 | Micheli | |
| 7,241,272 B2 | 7/2007 | Karoor | |
| 7,276,042 B2 | 10/2007 | Polaschegg | |
| 7,326,576 B2 | 2/2008 | Womble et al. | |
| 7,435,342 B2 | 10/2008 | Tsukamoto | |
| 7,488,447 B2 | 2/2009 | Sternby | |
| 7,537,688 B2 | 5/2009 | Tarumi et al. | |
| 7,544,300 B2 | 6/2009 | Brugger et al. | |
| 7,544,737 B2 | 6/2009 | Poss et al. | |
| 7,563,240 B2 | 7/2009 | Gross et al. | |
| 7,566,432 B2 | 7/2009 | Wong | |
| 7,597,806 B2 | 10/2009 | Uchi | |
| 7,794,419 B2 | 7/2010 | Paolini et al. | |
| 7,776,210 B2 | 8/2010 | Rosenbaum | |
| 7,850,635 B2 | 12/2010 | Polaschegg | |
| 7,922,686 B2 | 4/2011 | Childers et al. | |
| 7,922,911 B2 | 4/2011 | Micheli | |
| 7,947,179 B2 | 5/2011 | Rosenbaum | |
| 7,955,290 B2 | 6/2011 | Karoor et al. | |
| 7,988,854 B2 | 8/2011 | Tsukamoto | |
| 8,002,726 B2 | 8/2011 | Karoor | |
| 8,012,118 B2 | 9/2011 | Curtin | |
| 8,029,454 B2 | 11/2011 | Kelly et al. | |
| 8,066,658 B2 | 11/2011 | Karoor et al. | |
| 8,080,161 B2 | 12/2011 | Ding et al. | |
| 8,087,303 B2 | 1/2012 | Beavis | |
| 8,096,969 B2 | 1/2012 | Roberts | |
| 8,180,574 B2 | 5/2012 | Lo et al. | |
| 8,187,250 B2 | 5/2012 | Roberts | |
| 8,197,439 B2 | 6/2012 | Wang et al. | |
| 8,303,532 B2 | 11/2012 | Hamada et al. | |
| 8,404,491 B2 | 3/2013 | Ding et al. | |
| 8,409,444 B2 | 4/2013 | Wong | |
| 8,480,607 B2 | 7/2013 | Davies | |
| 8,647,506 B2 | 2/2014 | Wong | |
| 8,733,559 B2 | 5/2014 | Wong | |
| 8,764,981 B2 | 7/2014 | Ding | |
| 8,777,892 B2 | 7/2014 | Sandford | |
| 9,144,640 B2 | 9/2015 | Pudil | |
| 9,254,355 B2 | 2/2016 | Sandford | |
| 9,527,015 B2 | 12/2016 | Chau | |
| 2001/0007931 A1 | 7/2001 | Blatter | |
| 2002/0112609 A1 | 8/2002 | Wong | |
| 2002/0117436 A1 | 8/2002 | Rajan | |
| 2003/0080059 A1 | 5/2003 | Peterson et al. | |
| 2003/0097086 A1 | 5/2003 | Gura | |
| 2003/0105435 A1 | 6/2003 | Taylor | |
| 2003/0113931 A1 | 6/2003 | Pan | |
| 2003/0114787 A1 | 6/2003 | Gura | |
| 2004/0019312 A1 | 1/2004 | Childers et al. | |
| 2004/0099593 A1 | 5/2004 | DePaolis | |
| 2004/0147900 A1 | 7/2004 | Polaschegg | |
| 2004/0168963 A1 | 9/2004 | King | |
| 2004/0257409 A1 | 12/2004 | Cheok | |
| 2005/0006296 A1 | 1/2005 | Sullivan | |
| 2005/0056592 A1 | 3/2005 | Braunger | |
| 2005/0113796 A1 | 5/2005 | Taylor | |
| 2005/0150832 A1 | 7/2005 | Tsukamoto | |
| 2005/0274658 A1 | 12/2005 | Rosenbaum | |
| 2006/0241543 A1 | 10/2006 | Gura | |
| 2007/0007208 A1 | 1/2007 | Brugger et al. | |
| 2007/0179431 A1 | 8/2007 | Roberts | |
| 2007/0213665 A1 | 9/2007 | Curtin | |
| 2008/0006570 A1 | 1/2008 | Gura | |
| 2008/0011664 A1 | 1/2008 | Karoor | |
| 2008/0051696 A1 | 2/2008 | Curtin | |
| 2008/0053905 A9 | 3/2008 | Brugger et al. | |
| 2008/0217245 A1 | 9/2008 | Rambod | |
| 2009/0020471 A1 | 1/2009 | Tsukamoto | |
| 2009/0078636 A1 | 3/2009 | Uchi | |
| 2009/0101552 A1 | 4/2009 | Fulkerson | |
| 2009/0120864 A1 | 5/2009 | Fulkerson | |
| 2009/0157877 A1 | 6/2009 | Baek | |
| 2009/0216045 A1 | 8/2009 | Singh | |
| 2009/0266358 A1 | 10/2009 | Sacristan Rock | |
| 2010/0004588 A1 | 1/2010 | Yeh | |
| 2010/0007838 A1 | 1/2010 | Fujimoto | |
| 2010/0078381 A1 | 4/2010 | Merchant | |
| 2010/0078387 A1 | 4/2010 | Wong | |
| 2010/0084330 A1 | 4/2010 | Wong | |
| 2010/0100027 A1 | 4/2010 | Schilthuizen | |
| 2010/0101195 A1 | 4/2010 | Clements | |
| 2010/0102190 A1 | 4/2010 | Zhu et al. | |
| 2010/0114012 A1 | 5/2010 | Sandford | |
| 2010/0217181 A1 | 8/2010 | Roberts | |
| 2010/0224492 A1 | 9/2010 | Ding et al. | |
| 2010/0312172 A1 | 12/2010 | Hoffman | |
| 2010/0312174 A1 * | 12/2010 | Hoffman | A61M 1/1696 604/29 |
| 2010/0314314 A1 | 12/2010 | Ding | |
| 2011/0009798 A1 | 1/2011 | Kelly | |
| 2011/0017665 A1 | 1/2011 | Updyke | |
| 2011/0048949 A1 | 3/2011 | Ding et al. | |
| 2011/0163034 A1 | 7/2011 | Castellarnau | |
| 2011/0171713 A1 | 7/2011 | Bluchel | |
| 2011/0184340 A1 | 7/2011 | Tan | |
| 2011/0272352 A1 | 11/2011 | Braig | |
| 2011/0297593 A1 | 12/2011 | Kelly | |
| 2012/0018377 A1 | 1/2012 | Tsukamoto | |
| 2012/0248017 A1 | 10/2012 | Beiriger | |
| 2012/0273354 A1 | 11/2012 | Orhan et al. | |
| 2013/0018095 A1 | 1/2013 | Vath | |
| 2013/0019179 A1 | 1/2013 | Zhao | |
| 2013/0027214 A1 | 1/2013 | Eng | |
| 2013/0028809 A1 | 1/2013 | Barton | |
| 2013/0199998 A1 | 8/2013 | Kelly | |
| 2013/0213890 A1 | 8/2013 | Kelly | |
| 2013/0213891 A1 | 8/2013 | Karoor | |
| 2014/0001112 A1 | 1/2014 | Karoor | |
| 2014/0138294 A1 | 5/2014 | Fulkerson | |
| 2014/0158588 A1 | 6/2014 | Pudil | |
| 2014/0158623 A1 | 6/2014 | Pudil | |
| 2014/0190885 A1 | 7/2014 | Meyer | |

(56) References Cited

U.S. PATENT DOCUMENTS

| | | |
|---|---|---|
| 2014/0217028 A1 | 8/2014 | Pudil |
| 2014/0251908 A1 | 9/2014 | Ding |
| 2014/0326671 A1 | 11/2014 | Kelly |
| 2015/0057602 A1 | 2/2015 | Mason |
| 2015/0108069 A1* | 4/2015 | Merchant ............ A61M 1/1696 210/681 |
| 2015/0108609 A1 | 4/2015 | Kushida |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0251161 A1 | 9/2015 | Pudil |
| 2015/0251162 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |

FOREIGN PATENT DOCUMENTS

| | | |
|---|---|---|
| EP | 1592494 B1 | 6/2009 |
| EP | 2575827 A2 | 12/2010 |
| EP | 2576453 A2 | 12/2011 |
| EP | 2446908 | 5/2012 |
| EP | 1545652 B1 | 1/2013 |
| EP | 1345856 B1 | 3/2013 |
| EP | 2344220 B1 | 4/2013 |
| JP | 2981573 | 11/1999 |
| WO | 9532010 A1 | 11/1995 |
| WO | 0185295 A2 | 11/2001 |
| WO | 2002043859 | 6/2002 |
| WO | 2003043677 A2 | 5/2003 |
| WO | 2003051422 A2 | 6/2003 |
| WO | 2004064616 A2 | 8/2004 |
| WO | 2004062710 A3 | 10/2004 |
| WO | 2005123230 A2 | 12/2005 |
| WO | 2007089855 A2 | 8/2007 |
| WO | 2008075951 A1 | 6/2008 |
| WO | 2009157877 A1 | 12/2009 |
| WO | 2009157878 A1 | 12/2009 |
| WO | 2010028860 A1 | 2/2010 |
| WO | 2010102190 A4 | 11/2010 |
| WO | 2010141949 | 12/2010 |
| WO | WO 2011/017215 | 2/2011 |
| WO | 2013019179 | 2/2013 |
| WO | 2013019179 A1 | 2/2013 |
| WO | 2013025957 | 2/2013 |
| WO | 2013027214 | 2/2013 |
| WO | 2013028809 | 2/2013 |
| WO | 2013028809 A3 | 2/2013 |
| WO | 2013019994 A3 | 4/2013 |
| WO | 2012060700 | 5/2013 |
| WO | 2013025844 A3 | 5/2013 |
| WO | 2013101888 | 7/2013 |
| WO | 2013103607 A1 | 7/2013 |
| WO | 2013103906 | 7/2013 |
| WO | WO 2015060914 | 4/2015 |
| WO | 2015142624 | 9/2015 |
| WO | 2015-199863 | 12/2015 |
| WO | 2015-199864 | 12/2015 |
| WO | 2015199764 | 12/2015 |
| WO | WO 2015199765 | 12/2015 |

OTHER PUBLICATIONS

International Preliminary Report on Patentability for Application No. PCT/US2015/032492 dated Jun. 30, 2017.
International Preliminary Report on Patentability for Application No. PCT/US2015/016273 dated Feb. 19, 2016.
PCT Application, PCT/US20013/020404, filed Jan. 4, 2013.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
PCT/US2014/065950 International Search Report and Written Opinion dated Feb. 24, 2015.
PCT/US2015/032492 International Search Report dated Nov. 19, 2015.
PCT/US2015/016270 International Search Report and Written Opinion dated Jun. 5, 2015.
PCT/US2015/016273 International Search Report and Written Opinion dated Jun. 9, 2015.
PCT/US2015/032492 Written Opinion dated Nov. 19, 2015.
PCT/US2015/020046 International Search Report and Written Opinion dated Jun. 29, 2015.
International Search Report from PCT/US2012/051946.
U.S. Appl. No. 61/526,209.
U.S. Appl. No. 13/757,693, filed Jan. 4, 2013.
U.S. Appl. No. 13/836,079, filed Mar. 15, 2013.
U.S. Appl. No. 14/240,129, filed Aug. 22, 2013.
U.S. Appl. No. 13/835,735, filed Mar. 15, 2013.
PCT/US2015/020044 International Search Report Written Opinion dated Jun. 30, 2015.
PCT/US15/18587 International Preliminary Report on Patentability Dated Jun. 6, 2016.
[NPL548] PCT/US15/18587 International Preliminary Report on Patentability dated Jun. 6, 2016.
European Search Report for App. No. 15751391.2 dated Aug. 4, 2017.
European Search Report and supplementary Search Report for App. No. 14865374.4 dated Jun. 12, 2017.
[NPL10] Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
European Search Report for App. No. 15812081.6, dated Mar. 8, 2018.
European Search Report for EP App. No. 15811326.6, dated Feb. 14, 2018.
European Search Report for EP App. No. 15812413.1, dated Feb. 2, 2018.

* cited by examiner

MULTI-USE SORBENT CARTRIDGE

CROSS-REFERENCE

The present invention is a continuation-in-part (CIP) application of U.S. patent application Ser. No. 14/261,651, filed Apr. 25, 2014, which claims priority to U.S. Provisional Application No. 61/909,372 filed Nov. 26, 2013, and U.S. Provisional Application No. 61/941,672 filed Feb. 19, 2014, the contents of each incorporated herein in their entirety by reference.

FIELD OF THE INVENTION

The invention relates to a sorbent cartridge having one or more modules. The modules can be multi-use or single-use, and can be fluidly connected to a dialysis machine, or to a recharger for recharging the sorbent materials. Any one of the modules can be individually detachable from the sorbent cartridge body itself wherein the module can contain one or more sorbent materials such as zirconium phosphate, zirconium oxide, urease, alumina, activated carbon, among others. Certain sorbent materials can be placed relative to each other in specified positions downstream and upstream of each other to result in a configuration suitable for dialysis and for recharging the modules.

BACKGROUND

Sorbent cartridges can remove wastes from dialysate using less water than systems without sorbent cartridges. Sorbent cartridges operate by adsorbing ions and other waste species from a fluid. During dialysis, the dialysate fluid passes through a dialyzer and removes waste and solutes from one side of a semi-permeable membrane across a concentration and/or pressure gradient. The waste- and solute-containing dialysate can then be passed through the sorbent cartridge to remove waste and solutes. Depending on the amount of waste present in the cleaned dialysate, the dialysate can then be recirculated back to the dialyzer without requiring disposal.

Urease is used in the sorbent cartridge to catalyze urea into carbon dioxide and ammonium ions. The ammonium ions are then adsorbed by a cation exchange material downstream of the urease. One common cation exchange material is zirconium phosphate. However, zirconium phosphate can sometimes result in phosphate leakage. Phosphate anions present in the zirconium phosphate leak into the dialysate as the dialysate passes through the sorbent cartridge. Phosphate leakage can result in higher phosphate concentration in the dialysate, and reduce phosphate removal efficiency across the semi-permeable membrane.

The high cost of common sorbent materials such as zirconium phosphate and zirconium oxide is a significant limitation on sorbent dialysis. However, traditional sorbent cartridges are designed as single use devices and cannot be used for extended periods of time over many sessions and, critically, cannot be recharged to restore the functional capacity of the sorbent materials. Instead, traditional sorbent cartridges are discarded once the sorbent materials have been exhausted. Although traditional sorbent cartridges can be broken down to extract the sorbent materials for recharging, the sorbent materials must be re-processed at a processing plant, and cannot be recharged by the dialysis machine, a recharging device, or an in-clinic apparatus. The exhausted sorbent materials must be transported to a processing plant, the sorbent cartridge disassembled and the sorbent materials recharged by the plant. At some point, a new cartridge must be assembled and the recharged sorbent materials re-packaged into the cartridge and transported back to the dialysis clinic for use. As such, single- and limited-use sorbent cartridges drive up not only the unit cost of dialysis, but also the total cost of dialysis.

Compounding the cost problem, traditional cartridges cannot isolate specific materials into compartments for recharging. Certain materials such as urease and alumina may be cheaper than other sorbent materials such as zirconium phosphate and zirconium oxide. However, traditional cartridges cannot isolate and separate sorbent materials into different modules, compartments, or layers. In other words, traditional sorbent cartridges cannot be adapted to recharge certain expensive rechargeable sorbent materials such as zirconium oxide or zirconium phosphate because each component requires different recharging solutions, which perhaps ideal for washing one sorbent material, are destructive of another sorbent material. Finally, traditional cartridges cannot provide for specified positions of sorbent materials relative to each other. The placement of a sorbent material is particularly important for recharging insofar as each sorbent material can release ions impacting downstream sorbent materials. Also, placement of the sorbent materials can impact both upstream and downstream materials during cleaning if performed in a single flow path in a sorbent cartridge or a sorbent cartridge containing different types of sorbet materials.

Hence, there is a need for a rechargeable sorbent cartridge that does not need to be disassembled in order for the sorbent materials to be recharged. The sorbent cartridge should be rechargeable by the dialysis machine, a recharging station, or a suitably configured apparatus collocated with the dialysis clinic. The sorbent cartridge should provide for a separation of materials within the sorbent cartridge into modules, compartments, or layers, to allow for isolation of those materials to facilitate proper recharging without deleterious or unwanted effects. There is a need for a sorbent cartridge providing for isolation of one or more sorbent material to allow for cheaper or non-reusable materials to be discarded, while more expensive and reusable materials are recharged. There is a further need for a unitary sorbent cartridge having multiple discreet modules that can be easily connected and/or detachable from the unitary sorbent cartridge thereby facilitating the recharging and/or recycling of the sorbent materials and the sorbent cartridge while retaining a single unitary design.

There is also a need for a sorbent cartridge wherein the sorbent materials can be arranged within the modules of the cartridge to allow for isolation of particular materials or groups of materials. There is a further need for any one of the modules in the cartridge to be reusable or optionally detachable and re-attachable from the cartridge to allow any one of disposal, recycling, or recharging of sorbent material within the module. There is a need for a sorbent cartridge having specific materials that can be recharged and allowing for disposal of less expensive materials. There is a need to position sorbent materials relative to each other in order to facilitate in-sorbent recharging of exhausted materials and usage during dialysis, e.g., reducing the effects of phosphate leaching.

There is a further need for a system that can recapture phosphate that leaks into the dialysate from the zirconium phosphate sorbent layer. There is a further need for a modular sorbent cartridge, enabling isolation of particular sorbent materials to facilitate the recharging and reuse of these materials. The need also includes a multi-use zirconium phosphate module that can be positioned upstream of a multi-use zirconium oxide module to result in phosphate recapture.

SUMMARY OF THE INVENTION

The first aspect of the invention relates to a sorbent cartridge. In any embodiment of the first aspect of the invention, the sorbent cartridge can have at least one reusable module having one or more connectors fluidly connectable with a fluid flow path or fluidly connectable to a second module.

In any embodiment of the first aspect of the invention, the sorbent cartridge can comprise at least one non-reusable module. In any embodiment of the first aspect of the invention, the at least one reusable module can contain sorbent material. In any embodiment of the first aspect of the invention, the at least one reusable module can contain multiple sorbent materials. In any embodiment of the first aspect of the invention, the at least one non-reusable module can contain sorbent material. In any embodiment of the first aspect of the invention, the at least one non-reusable module can contain multiple sorbent materials.

In any embodiment of the first aspect of the invention, at least one module can be in fluid communication or be a part of a controlled compliant dialysis circuit. In any embodiment of the first aspect of the invention, the at least one reusable module can be connected with at least one other either reusable or non-reusable module. In any embodiment of the first aspect of the invention, the at least one reusable module can be detachable from the sorbent cartridge.

In any embodiment of the first aspect of the invention, the connectors can be selected from quick-connect, twist-lock, push-on, or threaded fittings. In any embodiment of the first aspect of the invention, the one or more connectors can comprise a length of tubing and a valve assembly.

In any embodiment of the first aspect of the invention, a connector can include an access point for a sensor. In any embodiment of the first aspect of the invention, a dialysis machine can comprise a connector. In any embodiment of the first aspect of the invention, the sorbent material can be selected from a group comprising zirconium phosphate, hydrous zirconium oxide, activated carbon, alumina, urease and ion exchange resin. In any embodiment of the first aspect of the invention, the ion-exchange resin can be selected to only remove calcium and magnesium ions by using a chelating ion exchange resin.

In any embodiment of the first aspect of the invention, the flow path can flow in a direction through a first module, through a connector, and then through a second module. In any embodiment of the first aspect of the invention, the flow path can flow in a direction through a first module, through a connector, through a second module, through a second connector and then through a third module. In any embodiment of the first aspect of the invention, a bypass flow path can divert flow from a first module to a third module. In any embodiment of the first aspect of the invention, a plurality of modules is contemplated including four or more modules.

In any embodiment of the first aspect of the invention, the flow can be diverted by a bypass flow path using a valve assembly positioned on a connector. In any embodiment of the first aspect of the invention, the valve assembly can be positioned on a connector after the first module and before the second module. In any embodiment of the first aspect of the invention, the valve assembly can be positioned on a connector after the second module and before the third module.

In any embodiment of the first aspect of the invention, a recharger can be positioned on the bypass flow path.

In any embodiment of the first aspect of the invention, a connector can connect in fluid communication any one or more of the modules of the invention to a recharger.

In any embodiment of the first aspect of the invention, the first module can contain hydrous zirconium oxide, alumina, urease and activated carbon, and the second module can contain zirconium phosphate.

In any embodiment of the first aspect of the invention, the first module can contain hydrous zirconium oxide, alumina, urease, zirconium phosphate and activated carbon, and the second module can contain zirconium phosphate. The respective layers can be formed into any combination of layers without restriction.

In any embodiment of the first aspect of the invention, the first module can contain hydrous zirconium oxide, alumina, urease, ion exchange resin and activated carbon, and the second module can contain zirconium phosphate. The respective layers can be formed into any combination of layers without restriction.

In any embodiment of the first aspect of the invention, the first module can contain alumina, urease, zirconium phosphate and activated carbon, and the second module can contain zirconium phosphate and hydrous zirconium oxide. The respective layers can be formed into any combination of layers without restriction.

In any embodiment of the first aspect of the invention, the first module can contain hydrous zirconium oxide, alumina, urease and activated carbon, and the second module can contain zirconium phosphate and ion exchange resin. The respective layers can be formed into any combination of layers without restriction.

In any embodiment of the first aspect of the invention, the first module can contain alumina, urease and activated carbon, and the second module can contain zirconium phosphate, ion exchange resin and hydrous zirconium oxide. The respective layers can be formed into any combination of layers without restriction.

In any embodiment of the first aspect of the invention, the first module can contain activated carbon, the second module can contain alumina and urease, and the third module can contain zirconium phosphate, ion exchange resin and hydrous zirconium oxide. The respective layers can be formed into any combination of layers without restriction.

In any embodiment of the first aspect of the invention, the first module can contain activated carbon, alumina, urease and hydrous zirconium oxide, the second module can contain zirconium phosphate, and the third module can contain zirconium phosphate and activated carbon. The respective layers can be formed into any combination of layers without restriction.

In any embodiment of the first aspect of the invention, the first module can contain activated carbon, the second module can contain alumina and urease, and the third module can contain zirconium phosphate, ion exchange resin and hydrous zirconium oxide. The respective layers can be formed into any combination of layers without restriction.

In any embodiment of the first aspect of the invention, the non-reusable module or modules can be disposable. In any embodiment of the first aspect of the invention, the reusable module or modules can be recyclable and/or recharged.

In any embodiment of the first aspect of the invention, at least one of the modules can have a barcode or other identification system. In any embodiment of the first aspect of the invention, two or more sorbent materials may be mixed together.

Any of the features disclosed above as being part of the first aspect of the invention can be included in the first aspect of the invention either alone or in combination.

The second aspect of the invention is directed to a method of recycling a reusable module. In any embodiment of the second aspect of the invention, the method can comprise the steps of disconnecting a reusable module from connectors connecting the reusable module to a non-reusable module, a bypass line and/or a wash line; removing the reusable module from a sorbent cartridge; emptying sorbent material from the reusable module; refilling the reusable module with new sorbent material; and reconnecting the reusable module to the connectors in the sorbent cartridge.

Any of the features disclosed above as being part of the second aspect of the invention can be included in the second aspect of the invention either alone or in combination.

The third aspect of the invention is directed to a method of replacing a detachable module that can be optionally reusable. In any embodiment of the third aspect of the invention, the method can comprise the steps of disconnecting a detachable module from connectors connecting the detachable module to another module that can be optionally reusable, a bypass line and/or a wash line; removing the detachable module from a sorbent cartridge; discarding the detachable module; and inserting and connecting a new module in the sorbent cartridge.

Any of the features disclosed above as being part of the third aspect of the invention can be included in the third aspect of the invention either alone or in combination.

The fourth aspect of the invention is directed to a method for recharging sorbent material within a reusable sorbent cartridge. In any embodiment of the fourth aspect of the invention, the method can comprise the steps of disconnecting a reusable module from connectors connecting the reusable module to another module, bypass line, and/or wash line; and connecting the reusable module to a recharger known to those of ordinary skill in the art. In any embodiment of the fourth aspect of the invention, the recharger can contain a fluid capable of recharging the sorbent material in the reusable module. In any embodiment of the fourth aspect of the invention, the method can further comprise the steps of passing the fluid from the recharger through the reusable module; and reconnecting the reusable module to the connectors in the sorbent cartridge.

In any embodiment of the fourth aspect of the invention, the reusable module can contain zirconium phosphate, and the recharger can contain a solution comprising sodium and hydrogen ions. In any embodiment of the fourth aspect of the invention, the reusable module can also contain ion exchange resin. In any embodiment, the reusable module can also contain hydrous zirconium oxide and the recharger can also contain acetate ions.

In any embodiment of the fourth aspect of the invention, the recharger can contain a first fluid. In any embodiment of the fourth aspect of the invention, the method for recharging sorbent material can further comprise the steps of passing the first fluid through the reusable module; replacing the first fluid with a second fluid; and passing the second fluid through the reusable module.

In any embodiment of the fourth aspect of the invention, the reusable module can contain activated carbon and the recharger can contain heated water. In any embodiment of the fourth aspect of the invention, the reusable module can contain alumina and urease and the first fluid can be heated water, and the second fluid can contain urease.

In any embodiment of the fourth aspect of the invention, the valve assembly can be operated under control of a programmable controller or computer system to regulate flow into, out of, and between modules. In any embodiment of the fourth aspect of the invention, fluid flow through the valve assembly can be sensed by a photocell or other flow sensing and/or measuring apparatus. In any embodiment of the fourth aspect of the invention, the sorbent cartridge can comprise a control pump for circulating fluid in the fluid flow path.

In any embodiment of the fourth aspect of the invention, the sorbent cartridge can have multiple modules including any one of 2, 3, 4, or 5 modules. In any embodiment of the fourth aspect of the invention, the modules can be connected by any of quick-connect, twist-lock, push-on, or threaded fittings, or a length of tubing. In any embodiment of the fourth aspect of the invention, the modules can be used multiple times and/or recharged. In any embodiment of the fourth aspect of the invention having multiple modules, the number of times the multiple modules can be used or recharged can be different from each other.

Any of the features disclosed above as being part of the fourth aspect of the invention can be included in the fourth aspect of the invention either alone or in combination.

The fifth aspect of the invention relates to a modular sorbent cartridge. In any embodiment of the fifth aspect of the invention, the sorbent cartridge can have a first module configured to contain urease and a second module that is fluidly connectable to the first module and downstream of the first module, the second module configured to contain a cation exchanger and also a third module fluidly connectable to the second module and downstream of the second module, the third module configured to contain an anion exchanger.

In any embodiment of the fifth aspect of the invention, the cation exchanger can be zirconium phosphate contained in the second module and the anion exchanger can be zirconium oxide contained in the third module.

In any embodiment of the fifth aspect of the invention, the first module can be single-use, the second module can be multi-use, and the third module can be multi-use.

In any embodiment of the fifth aspect of the invention, the first module can contains any one of activated carbon, ion exchange resin, alumina, urease, and combinations and mixtures thereof.

In any embodiment of the fifth aspect of the invention, the first module can have a first layer of activated carbon, a second layer of alumina and urease which can be downstream of the first layer, and a third layer of activated carbon which can be downstream of the second layer.

In any embodiment of the fifth aspect of the invention, a layer of zirconium oxide can be positioned downstream of the second layer and upstream of the third layer.

In any embodiment of the fifth aspect of the invention, the module comprising zirconium phosphate can be rechargeable, the module comprising zirconium oxide can be rechargeable, or both the module comprising zirconium phosphate and the module comprising zirconium oxide can be rechargeable.

In any embodiment of the fifth aspect of the invention, the first module can be fluidly connectable to a dialysate flow path upstream of the first module, and the third module can be fluidly connectable to a dialysate flow path downstream of the third module.

In any embodiment of the fifth aspect of the invention, zirconium oxide can be present both upstream and downstream of the zirconium phosphate.

In any embodiment of the fifth aspect of the invention, an amount of the zirconium oxide upstream of the zirconium phosphate can be less than an amount of the zirconium oxide downstream of the zirconium phosphate.

In any embodiment of the fifth aspect of the invention, the second module comprising the cation exchanger can be multi-use, and the third module comprising the anion exchanger can be multi-use.

In any embodiment of the fifth aspect of the invention, the second module can have the proviso that zirconium oxide and zirconium phosphate are not contained together in the same module.

In any embodiment of the fifth aspect of the invention, the second module does not comprise any other sorbent materials other than zirconium phosphate.

In any embodiment of the fifth aspect of the invention, a bypass flow path can fluidly connect a position upstream of the first module to the second module.

In any embodiment of the fifth aspect of the invention, the first module can have a first layer of activated carbon, and a second layer of alumina and urease downstream of the first layer, and the second module can have a first layer of alumina, a second layer of activated carbon downstream of the first layer, and a third layer of zirconium phosphate downstream of the second layer.

In an embodiment of the sixth aspect of the invention, a sorbent cartridge can have at least one module configured to contain a cation exchanger; and at least one module configured to contain an anion exchanger, wherein the module configured to contain the anion exchanger can be fluidly connectable to and downstream of the module configured to contain a cation exchanger.

In any embodiment of the sixth aspect of the invention, the cation exchanger can be zirconium phosphate and the anion exchanger can be zirconium oxide.

In any embodiment of the sixth aspect of the invention, the module configured to contain the cation exchanger and the module configured to contain the anion exchanger can be multi-use.

In any embodiment of the sixth aspect of the invention, the module configured to contain the cation exchanger and the module configured to contain the anion exchanger can be detachable.

In any embodiment of the sixth aspect of the invention, at least a second module upstream of the module configured to contain zirconium phosphate can contain any one of activated carbon, alumina, urease, and combinations thereof.

In any embodiment of the sixth aspect of the invention, the second module can further have zirconium oxide.

In any embodiment of the sixth aspect of the invention, an amount of the zirconium oxide in the second module can be less than an amount of the zirconium oxide downstream of the zirconium phosphate.

Any of the features disclosed above as being part of the fifth aspect of the invention can be included in the sixth aspect of the invention either alone or in combination.

DETAILED DESCRIPTION OF THE INVENTION

Figure 1:
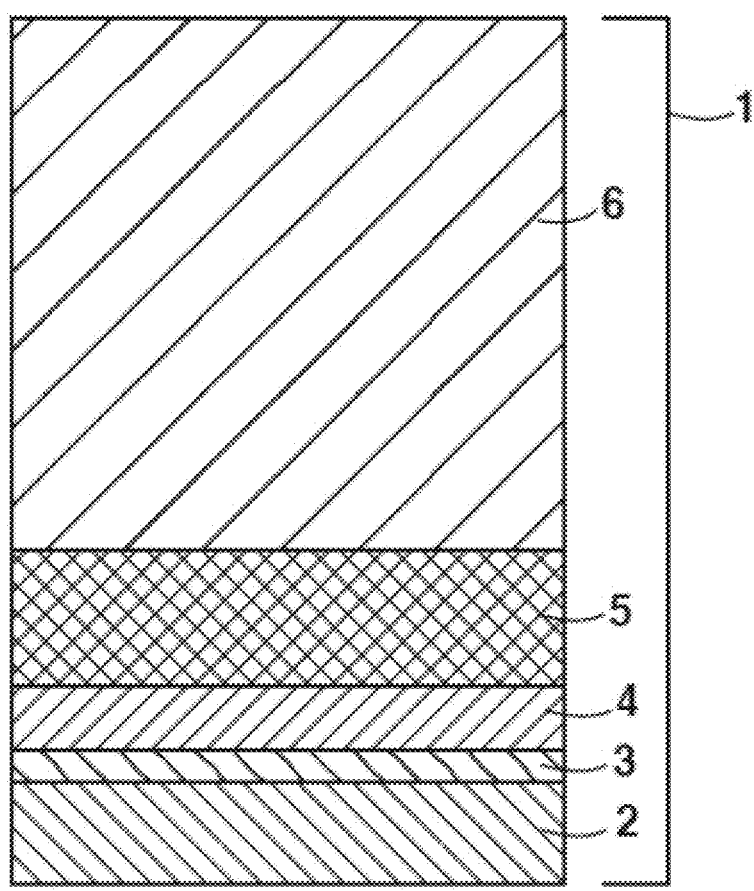
FIG. 1 shows a sorbent cartridge containing activated carbon, hydrous zirconium oxide, urease, alumina, and zirconium phosphate.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. For example, "an element" means one element or more than one element.

The term "anion exchanger" means a material that can bind a molecule having a negative charge and exchange another molecule having a negative charge for the bound molecule.

A "bar code" is a computer readable pattern of parallel lines and spaces of variable thickness that identifies the component to which the barcode is attached.

"Blow out" refers to the process of passing a gas through a connection line or a module.

"Bypass line," or "bypass flow path" refers to a line, connected to the main line, through which fluid or gas may alternatively flow.

The term "cartridge" refers to any container designed to contain a powder, liquid, or gas made for ready connection to a device or mechanism. The container can have one or more compartments. Instead of compartments, the container can also comprise system of two or more modules connected together to form the cartridge wherein the two or more modules once formed can be connected to a device, structure, flow path or mechanism.

The term "cation exchanger" means a material that can bind a molecule having a positive charge and exchange another molecule having a positive charge for the bound molecule.

The term "configured to contain" means any particular form, alignment, shape, design, marking, or arrangement suitable for an intended material to be contained therein.

The term "comprising" includes, but is not limited to, whatever follows the word "comprising." Use of the term indicates the listed elements are required or mandatory but that other elements are optional and may be present.

A "connector" describes the concept of forming a fluid connection between two components wherein fluid or gas can flow from one component, through a connector or a component for connection, to another component. The connector provides for a fluid connection in its broadest sense and can include any type of tubing, fluid or gas passageway, or conduit between any one or more components of the invention.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "controlled compliant flow path", "controlled compliant dialysate flow path" and "controlled compliant solution flow path" refer to flow paths operating within a controlled compliant system having the characteristic of controlled compliance, or of being controlled compliant as defined herein.

The terms "controlled compliance" and "controlled compliant" describe the ability to actively control the transfer of fluid volume into or out of a compartment, flow path or circuit. In certain embodiments, the variable volume of fluid in a dialysate circuit or controlled compliant flow path expands and contracts via the control of one or more pumps in conjunction with one or more reservoirs. The volume of fluid in the system is generally constant (unless additional fluids are added to a reservoir from outside of the system) once the system is in operation if patient fluid volume(s), flow paths, and reservoirs are considered part of the total volume of the system (each individual volume may sometimes be referred to as a fluid compartment). The attached reservoirs allow the system to adjust the patient fluid volume by withdrawing fluid and storing the desired amount in an attached control reservoir and/or by providing purified and/or rebalanced fluids to the patient and optionally removing waste products. The terms "controlled compliance" and "controlled compliant" are not to be confused with the term "non-compliant volume," which simply refers to a vessel, conduit, container, flow path, conditioning flow path or cartridge that resists the introduction of a volume of fluid after air has been removed from a defined space such as a vessel, conduit, container, flow path, conditioning flow path or cartridge. In any embodiment, the controlled compliant system can move fluids bi-directionally. In certain cases, the bi-directional fluid movement can be across a semi-permeable membrane either inside or outside a dialyzer. The bi-directional fluid flow can also occur across, through, or between vessels, conduits, containers, flow paths, conditioning flow paths or cartridges of the invention in selected modes of operation. The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow path or between a flow path and reservoir in a controlled compliant system.

A "control pump" means an apparatus capable of moving fluid through a system at a specific rate. The term "control pump," can include for example an "ultrafiltrate pump," which is a pump that is operable to pump fluid bi-directionally to actively control the transfer of fluid volume into or out of a compartment or circuit.

A "control system" consists of combinations of components that act together to maintain a system to a desired set of performance specifications. The control system can use processors, memory and computer components configured to interoperate to maintain the desired performance specifications. It can also include fluid or gas control components, and solute control components as known within the art to maintain the performance specifications.

A "controller," "control unit," "processor," or "microprocessor" is a device which monitors and affects the operational conditions of a given system. The operational conditions are typically referred to as output variables of the system wherein the output variables can be affected by adjusting certain input variables.

A "degasser" is a component that is capable of removing dissolved and undissolved gasses from fluids.

The term "detachable" or "detached" relates to any component of the present invention that can be separated from a system, module, cartridge or any component of the invention. "Detachable" can also refer to a component that can be taken out of a larger system with minimal time or effort. In certain instances, the components can be detached with minimal time or effort, but in other instances can require additional effort. The detached component can be optionally reattached to the system, module, cartridge or other component. A detachable module can often be part of a reusable module.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

"Dialysate" is the fluid that passes through the dialyzer on the side of the dialysis membrane opposite to the fluid (e.g. blood) being dialyzed.

The term "downstream," as used when referring to relative positions of components of a dialysis system, refers to a later position in the normal operational flow direction of the dialysis system. Fluid moving in the normal operation flow direction of the dialysis system will contact the "upstream" position first, and then the "downstream" position.

"Flow" refers to the movement of a liquid, gas, or both.

A "flow sensing apparatus" or "flow measuring apparatus" is an apparatus capable of measuring the flow of liquid or gas within a specific area.

A "fluid" is a liquid substance optionally having a combination of gas and liquid phases in the fluid. Notably, a liquid can therefore also have a mixture of gas and liquid phases of matter.

The term "fluid communication" refers to the ability of fluid or gas to move from one component or compartment to another within a system or the state of being connected, such that fluid or gas can move by pressure differences from one portion that is connected to another portion.

The term "fluidly connectable" refers to the ability to pass fluid or gas from one point to another point. The two points can be within or between any one or more of compartments, modules, systems, components, and rechargers, all of any type.

"Infusate" is a solution of one or more salts for the adjustment of the composition of a dialysate.

A "modular sorbent cartridge" is a sorbent cartridge that is made up of more than one individual modules, each containing one or more sorbent materials. The individual modules can be connected together to form the modular sorbent cartridge.

"Module" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for dialysis. In such a case, the module can comprise one or more compartments within the module. Alternatively, two or more modules can form a cartridge to be fitted to a device or mechanism where each module individually carries separate components but only when connected together contain in summation all the necessary components for an intended purpose such as a sorbent for dialysis. A module can be referred to as a "first module," "second module," "third module," etc. to refer to any number of modules. The designation of "first," "second," "third," etc. does not refer to the respective placement of the module in the direction of fluid or gas flow, and merely distinguishes one module from another unless otherwise indicated.

A "multi-use module" is a module that contains sorbent materials that can be recharged. The "multi-use" module can be used more than one time by recharging the rechargeable sorbent materials contained inside.

The term "non-reusable" refers to a component that cannot be reused in the component's current state. In certain instances, the term non-reusable can include the concept of being disposable, but is not necessarily limited to just being disposable.

An "operational line" is a line that directs fluid or gas in a path normally used while the system is in normal operation.

The terms "pathway," "conveyance pathway," "fluid flow path," and "flow path" refer to the route through which a fluid or a gas, such as dialysate or blood travels, or the route a gas travels.

A "photocell" is a sensor capable of measuring light or other electromagnetic radiation.

A "pressure valve" is a valve wherein, if the pressure of the fluid or gas passing the valve reaches a certain level, the valve will open to allow fluid or gas to pass through.

The term "pump" refers to any device that causes the movement of fluids or gases by the application of suction or pressure.

A "push-on fitting" is a fitting for connecting two components wherein the components may be connected by applying pressure to the base of the fitting attached to the components.

A "quick connect fitting" is a fitting for connecting two components wherein the male portion of the fitting contains flexible flanges extending outward with a portion on the end of the flange extending further outward, and the female portion of the fitting contains an internal ridge so that when connected, the outward extending portion of the flange sits under the ridge. By applying pressure, the flexible flange can be forced inward, past the ridge, enabling easy removal.

A "recharger" is a component that is capable of recharging spent sorbent material to or near its original state or usable capacity. A recharger may be part of the dialysis system or may be separate from the rest of the system. If the recharger is separate from the rest of the dialysis system, the term may include a separate facility where the spent sorbent material is sent to be returned to, or near, its original state.

"Recharging" refers to the process of treating a sorbent material to restore the functional capacity of the sorbent material so as to put the sorbent material back into a condition for use or reuse in a new dialysis session. In some instances recharging also includes treating a sorbent material so as to clean the sorbent material so that it can be stored and used in a subsequent dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged."

The term "recyclable" refers to a material that can be reused.

"Reusable" or "reusing" refers in one instance to a sorbent material, solid, liquid, or gas that can be used more than one time, optionally with treatment of any type of the material between uses. For example, a material and a solution can be reused. In one instance, reusable can refer to a sorbent cartridge that contains a sorbent material that can be recharged by recharging the sorbent material(s) within the sorbent cartridge A "sensor" is a component capable of determining the states of one or more variables in a system.

A "single-use module" is a module that contains sorbent materials not intended to be recharged even though the sorbent materials may functionally be rechargeable. The "single-use" module can be used more than one time, but requires replenishing or refilling of the sorbent materials inside. The terms replenishing or replenishing are to be distinguished from the term rechargeable, as used herein.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. When a single module contains all the sorbent materials necessary for performing dialysis, the single module can be referred to as a sorbent cartridge.

A "sorbent cartridge module" means a discreet component of a sorbent cartridge. Multiple sorbent cartridge modules can be fitted together to form a sorbent cartridge of two or more sorbent cartridge modules. In some embodiments, a single sorbent cartridge module can contain all of the necessary materials for dialysis. In such cases, the sorbent cartridge module can be considered to be a "sorbent cartridge."

"Sorbent materials" are materials capable of removing specific solutes from solution, such as urea.

A "sorbent module" is a container containing at least one sorbent material. In some embodiments, the sorbent module can connect to another sorbent module to form a sorbent cartridge.

"Spent dialysate" is a dialysate that has been contacted with blood through a dialysis membrane and contains one or more impurity, or waste species, or waste substance, such as urea.

"Tap water" refers to water obtained through piping from a water supply without additional treatment.

A "threaded fitting" is a fitting for connecting two components wherein the male portion has a helical ridge wrapped around a cylinder, and the female portion is a cylindrical hole with internal helical ridges so that when the male portion is screwed into the female portion the two components are locked together.

A "twist-lock fitting" is a fitting for connecting two components wherein the male portion of the fitting contains a head with a length exceeding its width, the female portion of the fitting is a hole with a length that exceeds its width and is larger than the male portion, so that when the male portion is inserted into the female portion and either portion is twisted the two components become locked together.

The term "upstream," as used when referring to relative positions of components of a dialysis system, refers to a prior position in the normal operational flow direction of the dialysis system. Fluid moving in the normal operation flow direction of the dialysis system will contact the "upstream" position first, and then the "downstream" position.

"Uremic toxins" are toxins carried in the blood supply normally removed in the kidneys.

A "valve" is a device capable of directing the flow of fluid or gas by opening, closing or obstructing one or more pathways to allow the fluid or gas to travel in a particular path. One or more valves configured to accomplish a desired flow can be configured into a "valve assembly."

A "wash line" is a line that directs fluid between a recharger and a module.

The term "waste fluid" refers to any fluid that does not have a present use in the operation of the system. Non-limiting examples of waste fluids include ultrafiltrate, or fluid volume that has been removed from a subject undergoing a treatment, and fluids that are drained or flushed from a reservoir, conduit or component of the system.

The terms "waste species," waste products," "waste," or "impurity species" refer to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system.

The term "water source" refers to a source from which potable or not potable water can be obtained.

Sorbent Dialysis

One non-limiting, exemplary sorbent cartridge is shown in FIG. 1. Spent dialysate can flow from the bottom of the sorbent cartridge 1 to the top of the cartridge. The first sorbent material the spent dialysate contacts can be activated carbon 2. Activated carbon will remove nonionic toxins from the fluid by adsorption. Creatinine, glucose, uric acid, β2-microglobulin and other non-ionic toxins, except urea, can be adsorbed onto the activated carbon, removing those toxins from the fluid. Other non-ionic toxins will also be removed by the activated carbon. The fluid then continues through the sorbent cartridge to the zirconium oxide layer 3. The zirconium oxide layer 3 can remove phosphate and fluoride anions, exchanging them for acetate anions. The fluid can continue to move through the sorbent cartridge into the alumina/urease layer 4. Urease can catalyze the reaction of urea to form ammonia and carbon dioxide. The result of this is the formation of ammonium carbonate. The phosphate anions present in the fluid can also be exchanged for hydroxide ions on the alumina. As the fluid continues through the sorbent cartridge, it reaches alumina layer 5. Alumina layer 5 can remove any remaining phosphate ions from the fluid and helps retain urease within the sorbent cartridge. However, alumina has a low capacity for phosphate, and hence significantly more alumina is required as compared to zirconium oxide. The last layer through which the fluid travels can be the zirconium phosphate layer 6. In the zirconium phosphate layer 6, ammonium, calcium, potassium and magnesium cations can be exchanged for sodium and hydrogen cations. Ammonium, calcium, potassium and magnesium ions all preferentially bind to the zirconium phosphate, releasing the hydrogen and sodium ions originally present in the layer. The ratio of sodium to hydrogen ions released depends on the ratio originally present in the zirconium phosphate layer 6, and is therefore controllable. The result of the fluid passing through the sorbent cartridge 1 is that the fluid be regenerated and form dialysate that can be safely passed back through a dialyzer to a patient. In any embodiment of the first, second, third, fourth, fifth, or sixth aspect of the invention, potassium, calcium and magnesium can be added to the clean dialysate to replace any ions which were removed by the sorbent cartridge. The ions can be added and or controlled via an infusate system that can be positioned on a section of the fluid flow path after the sorbent cartridge.

Zirconium phosphate and zirconium oxide can be used as ion-exchange materials during sorbent dialysis. Zirconium phosphate in the sodium or hydrogen form can serve as a cation exchanger and absorb cations such as ammonium, calcium, potassium, and magnesium. In exchange for absorbing cations, zirconium phosphate can releases other cations, such as sodium and hydrogen. Zirconium oxide in the acetate form can serve as an anion exchanger by binding to anions, such as phosphate and fluoride. In exchange, zirconium oxide can release acetate as the displaced anion. In the hydrous form, zirconium oxide can also adsorb metals such as iron, mercury, lead, and aluminum. Both zirconium oxide and zirconium phosphate are relatively expensive sorbent materials.

Figure 2:
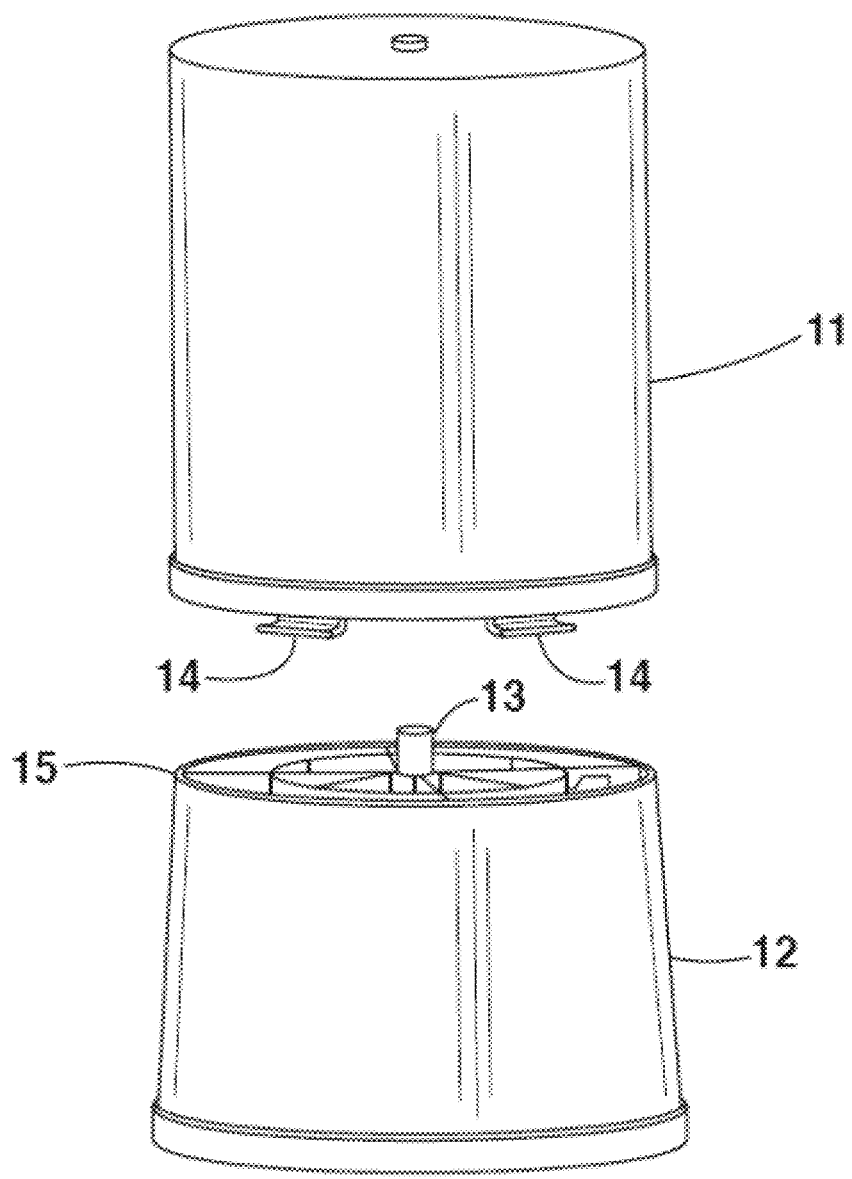
FIG. 2 shows a modular sorbent cartridge with two modules.

The first, second, third, fourth, fifth, or sixth aspect of the invention relate to a sorbent cartridge which includes at least one reusable module to advantageously recharge and reuse the materials. In any embodiment of the first, second, third, fourth, fifth, or sixth aspect of the invention, the reusable module 11 can be fluidly attached to a non-reusable module 12 by a connector 13 with the use of latches 14. The latches 14 can be integrally formed as part of the reusable module 11, non-reusable module 12, or may be a separate component that must be attached to either module as shown in FIG. 2. The latch members 14 can be mated to an annular connection ring 15 disposed on the circumference of module 12. One or more engagement members can be disposed inside the annular connection ring 15 to engage the latches 14 when positioned relative to each other using a radial motion. Such engagement can cause a rigid connection between the reusable module 11 and the non-reusable module 12. Other known locking or fastening mechanisms known to those of ordinary skill that can effectuate rapid and effective connections between two components are contemplated by the invention. Although only cylindrical modules are shown, it will be understood that modules of any shape such as rectangular, conical, triangular, etc. are contemplated by the first, second, third or fourth aspect of the invention with a correspondent fastening mechanism. It will be understood that different combinations of reusable and non-reusable modules can be combined together. In any embodiment of the first, second, third, fourth, fifth, or sixth aspect of the invention, both modules may be reusable or both may be non-reusable. Moreover, any one of the modules can be detachable from each other or from a casing forming the body of the sorbent cartridge. The modules can be standardized components that are interchangeable with other modules and easily assembled. For example, the latches 14 in FIG. 2 allow for a simple, twist-lock between two modules. The twist lock allows for the modules to be connected to each other by an easy and rapid manual motion not requiring complex maneuvering of the modules. The connection, once made, can be resistant to inadvertent disengagement, but can also be readily disengaged when desired with a similar easy and rapid manual manipulation. For example, a force applied on the outside periphery of the modules near the latch, e.g. squeezing the module, can cause the latch member 14 to disengage from the engagement members. In other examples the first, second, third, fourth, fifth, or sixth aspects of the invention, the modules can be disengaged by simply rotating the modules relative to each other.

In any embodiment of the first, second, third, fourth, fifth, or sixth aspects of the invention, each module can function as a sorbent cartridge independently. In any embodiment of the first, second, third, fourth, fifth, or sixth aspects of the invention, at least two modules can cooperate together when engaged to each other using, for example the latches 14 in FIG. 2 and being fluidly connected together to function as a sorbent cartridge. The advantage of such a modular design as described herein is that different sorbent materials can be dispersed between the at least two modules to allow for any particular sorbent or combination of sorbent materials to be detachable from a sorbent cartridge.

The connector 13 can be formed as part of the module and need not be a separate component that must be attached to the module 12. Rather, the connector 13 can be molded as part of the reusable module 12 and the non-reusable module 11. In any embodiment of the first, second, third, fourth, fifth, or sixth aspects of the invention, the connector can be affixed by mechanical means, glued or rigidly interfaced to the modules 11 and 12. The connector can be a combination of female and male connectors on a module. For example, a female connector can be disposed on one module, and a male connector on the other to form one connector 13 (not shown). In any embodiment of the first, second, third, fourth, fifth, or sixth aspects of the invention, the connector 13 allows fluid to flow into the non-reusable module 11, through the connector 13, into the reusable module 12. Alternatively, the connector 13 is not a part of either the non-reusable module 11 or reusable module 12 but can be a separate component such as tubing. It will be understood that the connector 13 is defined in its broadest sense and encompasses any fluid connection between two points.

One or more fluid connectors can be arranged between any module of the first, second, third, fourth, fifth, or sixth aspects of the invention, and one or more such fluid connectors can be provided in any of the described configurations herein. For example, a reusable module can have any number of connectors such as 1, 2, 3, 4, 5, or more. The spacing and distribution of the fluid connectors on the module can be positioned to enable and/or increase flow of fluid between the modules. In one example of the first, second, third, fourth, fifth, or sixth aspects of the invention, the fluid connectors can be spaced equidistant from each other or may be located axially or radially. Moreover, the sorbent cartridge may have one or more modules each having any number of connectors. In contrast to known sorbent cartridges having a unitary design in which sorbent materials are arranged in layers without any connectors between such layers, the fluid connectors of the first, second, third, fourth, fifth, or sixth aspects of the invention allow for controlled fluid or gas flow to any particular sorbent or combination of sorbent materials. The fluid connectors of the first, second, third, fourth, fifth, or sixth aspects of the invention also allow for any particular sorbent or combination of sorbent materials to be detachable from a sorbent cartridge. For example, a detachable module can be constructed with one or more sorbent materials. The detachable module can then be fluidly connected to the sorbent cartridge by fluid connectors. Such a configuration advantageously allows for separate treatment, recycling, or recharging of the sorbent or combination or mixture of sorbent materials not possible with known sorbent cartridges. In particular, known sorbent cartridges have all the sorbent materials being formed into layers or a plurality of sorbent materials being mixed without connectors in between such layers of one sorbent material, or mixtures of sorbent materials. Hence, it will be understood that the fluid connectors of the first, second, third, fourth, fifth, or sixth aspects of the invention can be critical in that the connectors control the order of sorbent materials to which a fluid or gas is exposed to, the delivery of fluid or gas to a particular sorbent or combination of sorbent materials, and the flow and rate of flow of a fluid or gas to various sorbent materials, layers or sorbent materials, and combination or mixtures of sorbent materials.

It will be understood that the first, second, third, fourth, fifth, or sixth aspects of the invention are distinct from known dialysis systems requiring separate housings containing sorbent materials that do not form a unitary sorbent cartridge for ready attachment or insertion into a dialysis machine. A unitary sorbent cartridge of the first, second, third, fourth, fifth, or sixth aspects of the invention contain each one of the sorbent materials described herein including cation and anion exchange resins inside the sorbent cartridge. In other words, the cation and anion exchange resins (or other sorbent materials) are not separated into another housing outside the sorbent cartridge. Although the individual sorbent materials of the first, second, third, fourth, fifth, or sixth aspects of the invention may be separated into different detachable and/or reusable modules within the single sorbent cartridge wherein each module is connected by fluid connectors, the single sorbent cartridge design provides reduced size and weight that is not possible with the known dialysis systems having separate housings. The modules, as described herein, can also be further rigidly fixed to each other by latches and engagement members or any fixing or fastening mechanism known to those of ordinary skill in the art. Notably, the sorbent cartridge of the first, second, third, fourth, fifth, or sixth aspects of the invention can have all of the sorbent materials described herein including cation and anion exchange resins within a single unitary sorbent cartridge for convenient removal, service and monitoring. In particular, the sorbent cartridge can have a single compartmental design wherein all sorbent materials necessary for performing dialysis are contained within a single compartment. The sorbent cartridge can also have a modular design wherein the sorbent materials are dispersed across at least two different modules, which can be connected to form a unitary body. Once the at least two modules are connected together, the connected modules can form a sorbent cartridge to be fitted to a device or mechanism. Advantageously, the sorbent cartridge of the first, second, third, fourth, fifth, or sixth aspects of the invention therefore can be easier to recycle, recharge, dispose of, service and remove from a dialysis machine. In any embodiment of the first, second, third, fourth, fifth, or sixth aspects of the invention, the unitary design can also provide for a compact design that can be used in a portable dialysis machine.

In any embodiment of the first, second, third, fourth, fifth, or sixth aspects of the invention, the fluid connector can be a quick-connect, twist-lock, push-on, or threaded fitting. Other forms of such connection known to those of ordinary skill in the art are contemplated by the present invention. Additionally, the connector can comprise a length of tubing and a valve assembly. In any embodiment of the first, second, third, fourth, fifth, or sixth aspects of the invention, the connector can be manually assembled to connect any component or assembly of the invention. The connector can also be used to rigidly connect any one of the modules to a recharger as defined herein when a separate fastening mechanism is not provided.

In any embodiment of the first, second, third, fourth, fifth, or sixth aspects of the invention, at least one module can be in fluid communication with a controlled compliant dialysis circuit as disclosed in U.S. patent application Ser. No. 13/565,733, the contents of which are incorporated herein in their entirety.

Figure 3:
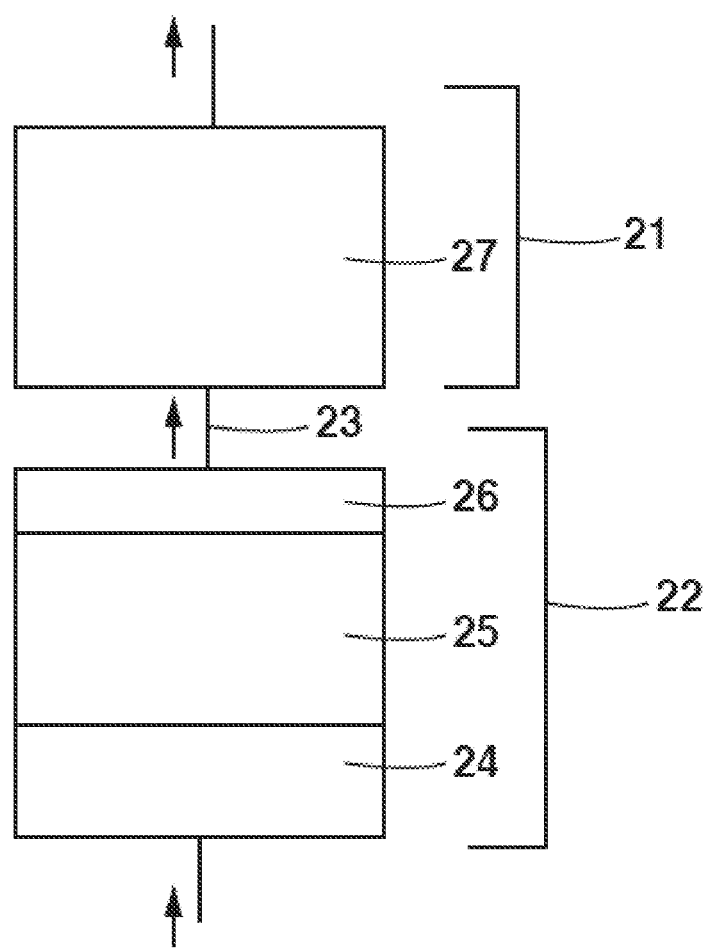
FIG. 3 shows a modular sorbent cartridge with two modules including activated carbon, alumina, urease, and zirconium oxide in the first module and zirconium phosphate in the second module.

It will be understood that the connector provides for a fluid connection in its broadest sense and can include any type of tubing, fluid or gas passageway, or conduit between any one or more components of the invention One embodiment of the modular sorbent cartridge of the first, second, third, fourth, fifth, or sixth aspects of the invention are shown in FIG. 3. The non-reusable module 22 of the sorbent cartridge can contain layers of activated carbon 24, alumina/urease 25, and hydrous zirconium oxide 26. The reusable module 21 contains zirconium phosphate 27.

After dialysis is complete, the zirconium phosphate layer 27 can contain ammonium, calcium, potassium and magnesium. The module 21 containing the zirconium phosphate may be removed, and the zirconium phosphate can be recharged. The reusable module 21 can be disconnected from the connectors 23 connecting the reusable module to the non-reusable module, bypass line and/or wash line. The reusable module 21 is then removed from the modular sorbent cartridge. This module can then be recharged, discarded and replaced, or alternatively, the sorbent material within the module can be removed and refilled. It will be understood that any one of the materials used in the first, second, third, fourth, fifth, or sixth aspects of the invention can be used multiple times. In such instances of multi-session use, the number of sessions that one component can be used, can be the same or different from the number of sessions that another component can be used. In one non-limiting example of the first, second, third, fourth, fifth, or sixth aspects of the invention, a module containing urease may be used 2 times while another module containing zirconium phosphate can be used 3 times. In other cases, the module containing urease can be used 3 times, and the module containing zirconium phosphate used 2 times. It will be understood that there is no limitation on the numbers of uses for any multi-session use module as compared to another module used in the sorbent cartridge.

Figure 4:
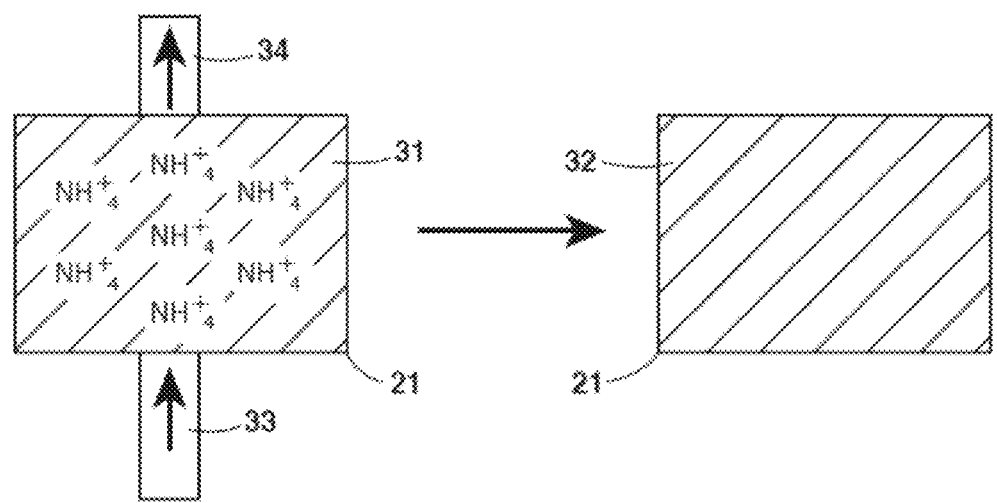
FIG. 4 shows a method for recharging the zirconium phosphate sorbent material.

The method of recharging the zirconium phosphate in a sorbent module of the first, second, third, or fourth aspects of the invention is shown in FIG. 4. Wash fluid 33, containing sodium and hydrogen ions, can be passed through the reusable module 21, containing the used zirconium phosphate 31 with bound ammonium ions. This causes an exchange of ions, wherein hydrogen and sodium ions can replace the ammonium ions on the zirconium phosphate 31. The waste fluid exiting the module 34 thus contains the freed ammonium ions, with excess sodium and hydrogen ions. This process creates a recharged zirconium phosphate layer 32, containing sodium and hydrogen ions for a subsequent dialysis. In any embodiment of the first, second, third, fourth, fifth, or sixth aspects of the invention, a recharger can be used to restore spent sorbent material wherein the recharger contains fluid capable of restoring spent sorbent material to its original state.

Figure 5:
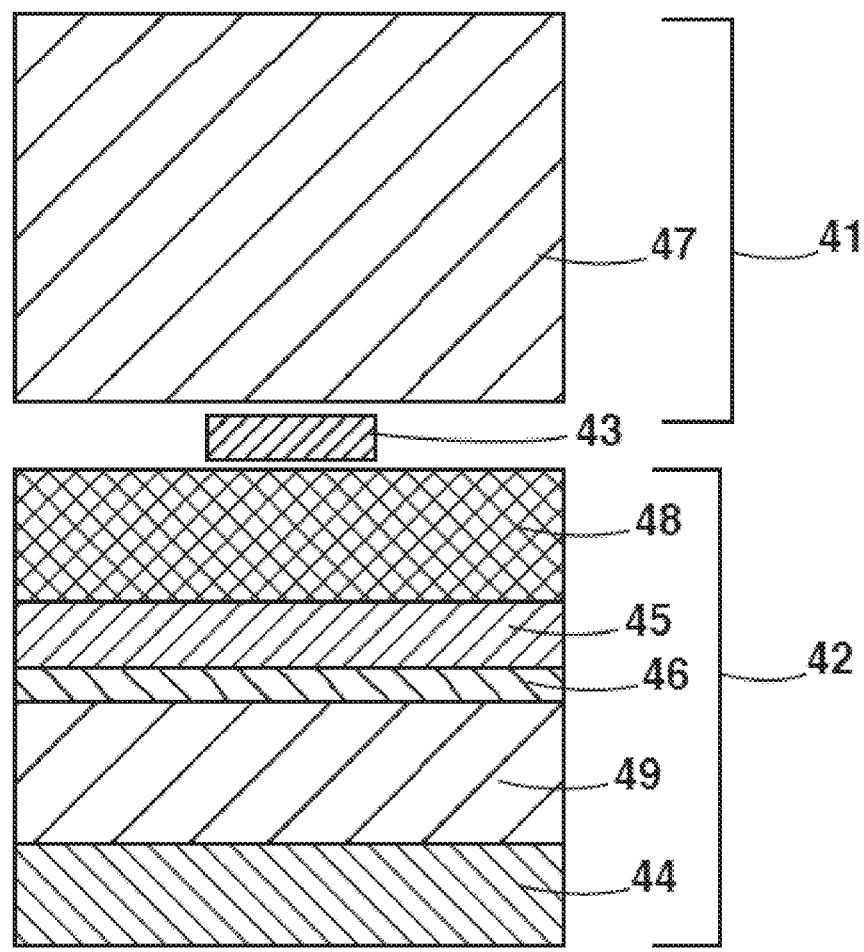
FIG. 5 shows a modular sorbent cartridge with two modules including activated carbon, zirconium phosphate, urease, alumina, and hydrous zirconium oxide in the first module and zirconium phosphate in the second module.

Because calcium and magnesium ions may be more difficult to remove from the zirconium phosphate, and therefore the zirconium phosphate may be more difficult to recharge, it may be advantageous to remove the calcium and magnesium in the first, non-reusable module, so that none of those ions need to be removed in the reusable zirconium phosphate module. Such an embodiment of the first, second, third, fourth, fifth, or sixth aspects of the invention are shown in FIG. 5. Spent dialysate enters the first, non-reusable module 42 where the dialysate can first flow through a layer of activated carbon 44 to remove non-ionic uremic toxins. The dialysate can then enter into a first layer of zirconium phosphate 49. This layer can remove the calcium, magnesium and potassium from the fluid. Next the fluid enters the hydrous zirconium oxide layer 46, which removes the phosphate anions and exchanges them with acetate anions. The fluid can then enter the urease layer 45 and alumina layer 48, where the urea is converted to ammonium carbonate and any remaining phosphate ions are removed. In any embodiments of the non-reusable module of the first, second, third, fourth, fifth, or sixth aspects of the invention, any arrangement of the activated carbon, zirconium phosphate, hydrous zirconium oxide layer, and urease and alumina layer is contemplated. For example, the dialysate can first flow through a first layer of zirconium phosphate, activated carbon, then the hydrous zirconium oxide layer, and then enter the urease layer and alumina layer. Alternatively, the dialysate can first flow through the hydrous zirconium oxide layer, then a first layer of zirconium phosphate, the activated carbon, then enter the urease layer and alumina layer. Still further, the dialysate can first flow through the urease layer and alumina layer, then the hydrous zirconium oxide layer, then a first layer of zirconium phosphate, and then the activated carbon. The fluid then flows through the connector 43, and into the second, reusable, sorbent module 41. This sorbent module can contain zirconium phosphate 47. Zirconium phosphate layer 47 can exchange the ammonium ions for sodium and hydrogen. Because the calcium, magnesium and potassium ions have already been removed by the first zirconium phosphate layer 49, this second layer 47 will not pick up those ions. After dialysis, the second module 41 will only contain zirconium phosphate bound to ammonium ions. As such, the dialysate may be easier to recharge.

In any embodiment of the first, second, third, fourth, fifth, or sixth aspects of the invention where the reusable module contains zirconium phosphate and ion-exchange resin, or zirconium phosphate and hydrous zirconium oxide, the module may be recharged in the same manner. The activated carbon layer of a reusable module can be recharged by passing a heated water solution through the module. The alumina/urease layers can be recharged by first passing heated water, or the solutions described above for recharging zirconium phosphate, through the layer, and then passing a solution containing urease through it.

Figure 6:
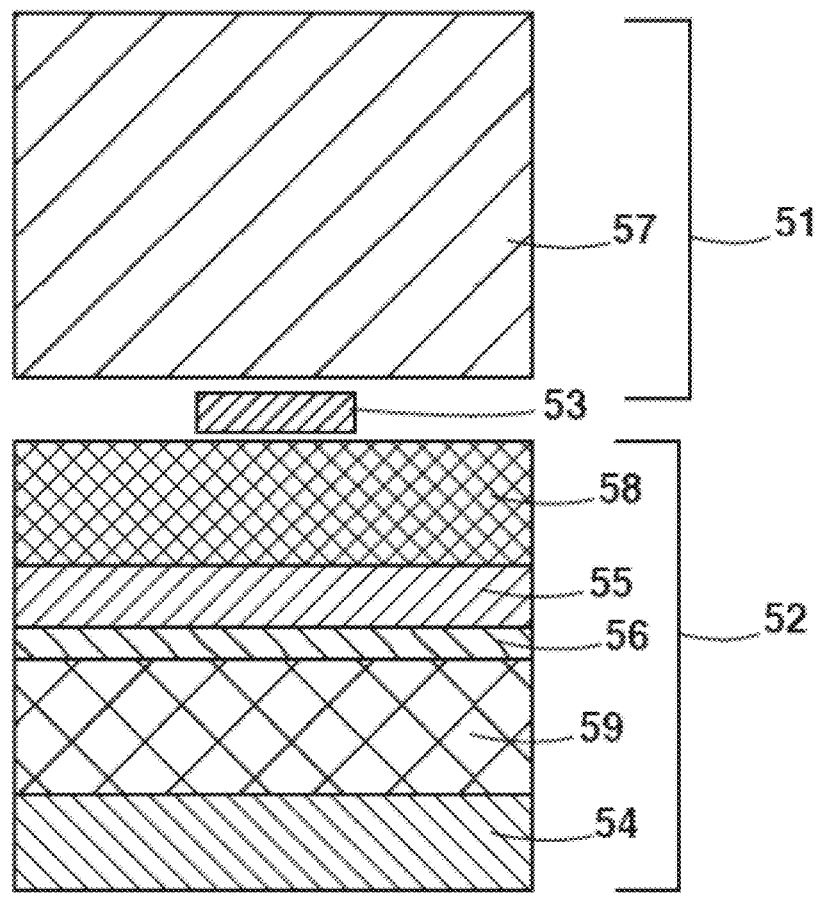
FIG. 6 shows a modular sorbent cartridge with two modules including activated carbon, ion exchange resin, alumina, urease, and hydrous zirconium oxide in the first module and zirconium phosphate in the second module.

Another non-limiting embodiment of the first, second, third, fourth, fifth, or sixth aspects of the invention are shown in FIG. 6. Spent dialysate can enter the first, non-reusable, module 52 where it first flows through a layer of activated carbon 54 to remove non-ionic uremic toxins. It then enters into a layer of ion exchange resin 59. Ion exchange resin layer 59 can remove the calcium, magnesium and potassium from the fluid. Next the fluid can enter the hydrous zirconium oxide layer 56, which removes the phosphate anions and exchanges them with acetate anions. The fluid then enters the urease layer 55 and alumina layer 58, where the urea is converted to ammonium carbonate and any remaining phosphate ions are removed. In any embodiment of the first module of the first, second, third, fourth, fifth, or sixth aspects of the invention, any arrangement of the activated carbon, ion exchange resin, hydrous zirconium oxide layer, and urease and alumina layer is contemplated. For example, the dialysate can first flow through an ion exchange resin, activated carbon, then the hydrous zirconium oxide layer, and then enter the urease layer and alumina layer. Alternatively, the dialysate can first flow through the hydrous zirconium oxide layer, then the ion exchange resin, the activated carbon, then enter the urease layer and alumina layer. Still further, the dialysate can first flow through the urease layer and alumina layer, then the hydrous zirconium oxide layer, then the ion exchange resin, and then the activated carbon. The fluid can then flow through the connector 53, and into the second, reusable, sorbent module 51. The sorbent module 51 contains zirconium phosphate 57. The zirconium phosphate layer 57 can exchange the ammonium ions for sodium and hydrogen. Because the calcium, magnesium and potassium ions have already been removed by the ion-exchange resin layer 59, the zirconium phosphate layer 57 will not pick up those ions. Alternatively, the ion-exchange resin 59 may be selected to only remove the calcium and magnesium ions, such as by using a chelating ion exchange resin. This can allow use of less of the ion exchange resin. If such a resin is used, the potassium will be removed by the zirconium phosphate 57. Potassium can be easier to remove from zirconium phosphate than calcium or magnesium.

One skilled in the art will recognize that different combinations of sorbent materials in both the reusable and non-reusable modules of the sorbent cartridge of the first, second, third, fourth, fifth, or sixth aspects of the invention can be used without being beyond the scope of this invention. The sorbent materials described herein can be mixed together in any combination as shown in the specific embodiments of the invention.

Figure 7:
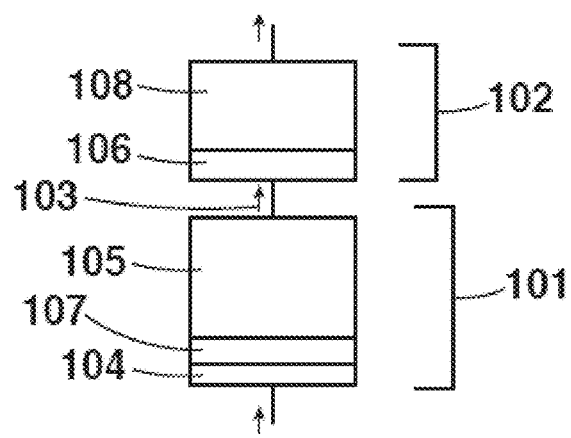
FIG. 7 shows a modular sorbent cartridge with two modules including activated carbon, alumina, urease, and zirconium phosphate in the first module and hydrous zirconium oxide and zirconium phosphate in the second module.

In any embodiment of the first, second, third, fourth, fifth, or sixth aspects of the invention, the sorbent cartridge can be removed from a dialysis system. The sorbent cartridge once removed can be separated into one or more modules to be recharged, disposed of, or recycled. For example, FIG. 7 shows an embodiment of the first, second, third, fourth, fifth, or sixth aspects of the invention wherein the reusable module contains both hydrous zirconium oxide and zirconium phosphate. The spent dialysate can enter the first module 101. The spent dialysate can first pass through the activated carbon layer 104. The spent dialysate can next pass through a first layer of zirconium phosphate 107, which removes the potassium, calcium and magnesium from the dialysate. Next the spent dialysate can moves through the alumina/urease layer 105. The fluid can then pass through the connector 103, and into the second module 102. The second module 102 contains a hydrous zirconium oxide layer 106, and a second zirconium phosphate layer 108, which removes the ammonium ions from the fluid. After dialysis, the reusable module 102 containing the hydrous zirconium oxide and zirconium phosphate can be recharged, discarded, or the sorbent material removed and new material added.

Figure 8:
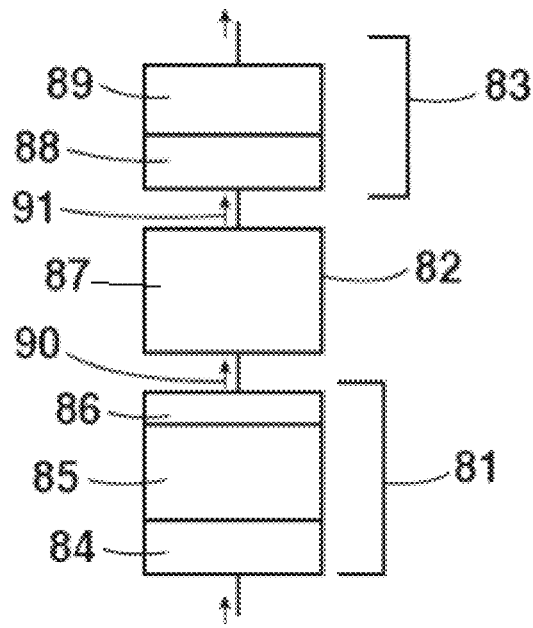
FIG. 8 shows a modular sorbent cartridge with three modules including activated carbon, alumina, urease, and hydrous zirconium oxide in the first module, zirconium phosphate in the second module, and zirconium phosphate and activated carbon in the third module.

One skilled in the art will realize that embodiments of the first, second, third, fourth, fifth, or sixth aspects of the invention can be included that involve the sorbent materials being mixed within the module, as opposed to arranging the materials in layers. Such mixing of the sorbent materials can be performed interspersing the sorbent materials in a single layer by any method known to those of skill in the art. The modular sorbent cartridges of the first, second, third, fourth, fifth, or sixth aspects of the invention are not limited to having two modules. Any number of modules may be utilized in this invention. A three module sorbent cartridge is shown in FIG. 8. The first module 81 contains a layer of activated carbon 84, a layer of alumina/urease 85, and a layer of hydrous zirconium oxide 86. The described layers can also be mixed together rather than being provided in layers. In any embodiment of the first, second, third, fourth, fifth, or sixth aspects of the invention, in the first module of a three module sorbent cartridge, any arrangement of the activated carbon, hydrous zirconium oxide layer, and urease and alumina layer is contemplated. For example, the dialysate can first flow through activated carbon, then the hydrous zirconium oxide layer, and then enter the urease layer and alumina layer. Alternatively, the dialysate can first flow through the hydrous zirconium oxide layer, then the activated carbon, then enter the urease layer and alumina layer. Still further, the dialysate can first flow through the urease layer and alumina layer, then the hydrous zirconium oxide layer, and then the activated carbon. Again, the described arrangements include not just layers, but also intermixed sorbent materials. The fluid, after passing through these layers, passes through a first connector 90, and into the second module 82. This second module 82 can contain zirconium phosphate 87. The fluid can then pass through a second connector 91, and enter a third module 83.

This third module can contain a second layer of zirconium phosphate 88, and a second layer of activated carbon 89 for final purification before passing out of the sorbent cartridge. In any embodiment of the first, second, third, fourth, fifth, or sixth aspects of the invention, in the third module of a three module sorbent cartridge, any arrangement of the activated carbon and the second layer of zirconium phosphate are contemplated. For example, the dialysate can first flow through activated carbon and then the second layer of zirconium phosphate. It will be understood that any number of modules can be configured in the first, second, third, fourth, fifth, or sixth aspects of the invention. For example, a sorbent cartridge having four, five, six, seven, or more modules is contemplated by the invention. It will be understood that the described arrangements include not just layers, but also the sorbent materials being intermixed.

As each layer of sorbent material within the modular sorbent cartridge may be recharged, a cartridge is possible where all of the modules are reusable. It is still advantageous to utilize separate modules for the sorbent materials in order to direct the correct recharging solution through the correct module, and because different sorbent materials may need to be replaced more often than others.

Because the ability for the zirconium phosphate layer to bind ammonium ions is finite, while the capacity of the urease layer to break down urea into ammonia is not, the capacity of the zirconium phosphate layer may be exceeded. In such a case, excess ammonium ions can be caused to pass through the sorbent cartridge and remain in the dialysate. To protect patient safety, once ammonia breakthrough has occurred, either dialysis session can be stopped or at least urease can be prevented from catalyzing the conversion of urea to ammonia.

Figure 9:
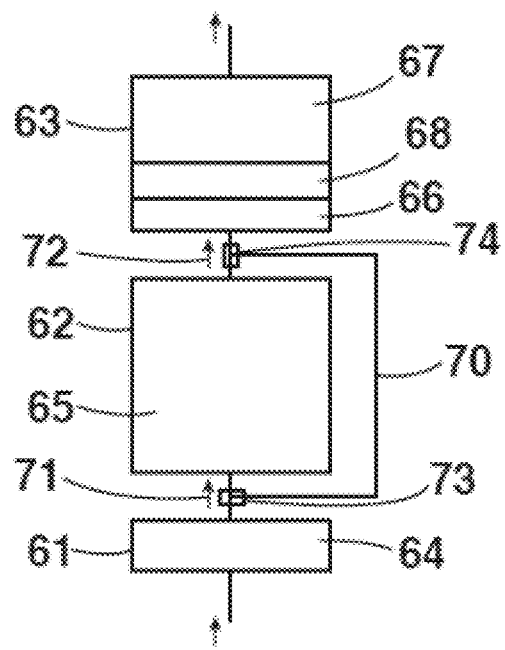
FIG. 9 shows a modular sorbent cartridge with three modules including activated carbon in the first module, alumina and urease in the second module, and ion-exchange resin, zirconium phosphate, and hydrous zirconium oxide in the third module, with an optional bypass line to direct fluid from the first to the third modules.

FIG. 9 shows a three-module sorbent cartridge of the first, second, third, fourth, fifth, or sixth aspects of the invention that can allow bypass of the alumina/urease layer in the case of ammonia breakthrough. Ammonia breakthrough can occur when the capacity of the zirconium phosphate layer to exchange ammonium ion is exceeded. In the event of ammonia breakthrough, the spent dialysate can enter the first module 61, which contains the activated carbon layer 64. The spent dialysate then passes through a first connector 71, and by-pass flow valve 73. In normal operation, the flow valve 73 can be set to allow the fluid to pass into the second module 62. The second module can contain alumina/urease layer 65, which catalyzes the breakdown of urea into ammonium ions. The fluid then passes through the second connector 72, by the second valve 74, and into the third module 63. The third module can contain a hydrous zirconium oxide layer 66, ion-exchange resin 68, and zirconium phosphate layer 67. In any embodiment of the first, second, third, fourth, fifth, or sixth aspects of the invention having three modules, the third module can have any arrangement of the ion-exchange resin, hydrous zirconium oxide layer, and zirconium phosphate. For example, the dialysate can first flow through ion-exchange resin, then the hydrous zirconium oxide layer, and then enter the zirconium phosphate layer. Alternatively, the dialysate can first flow through the hydrous zirconium oxide layer, then the ion-exchange resin, then enter zirconium phosphate layer. Still further, the dialysate can first flow through the zirconium phosphate layer, then the hydrous zirconium oxide layer, and then the ion-exchange resin. Again, the described arrangements include not just layers, but also intermixed sorbent materials. After passing through the third module, a regenerated dialysate can exit the sorbent cartridge. In the event of ammonia breakthrough, the first valve 73 can be set to redirect the fluid into bypass line 70. This line will cause the fluid not to enter the second module 62, and therefore the urea will not be broken down into ammonia in the alumina/urease layer. The fluid will instead be directed to the second valve 74, where the fluid enters the second connector 72, and then the third module 63. In this way dialysis may continue, while avoiding the creation of ammonia. The valve assembly can, in any embodiment of the first, second, third, fourth, fifth, or sixth aspects of the invention, also include an access point for a sensor. The access point can be a portion of the valve assembly wherein a sensor can contact the fluid to take measurement data such as a flow or pressure reading. The form and construction of such access points contemplated by the present invention are those known to one of ordinary skill in the art.

Figure 10:
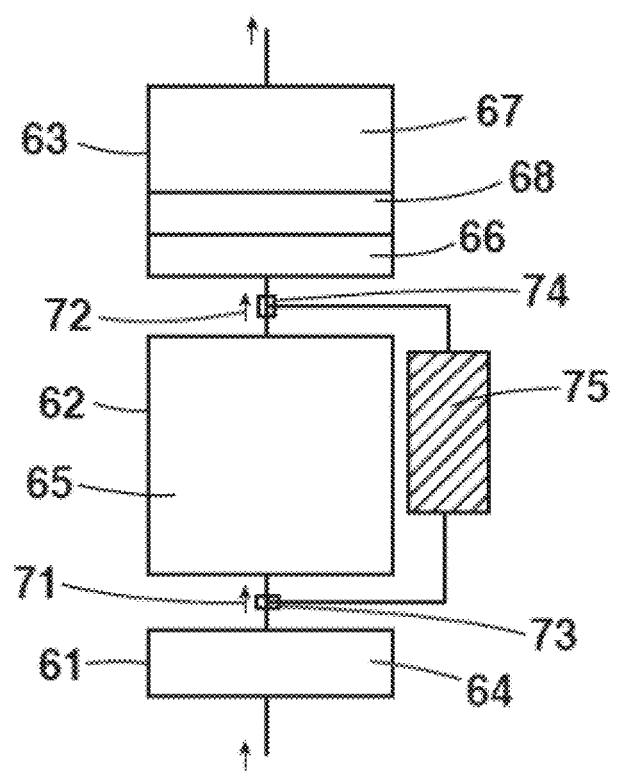
FIG. 10 shows a modular sorbent cartridge with three modules with an optional bypass line connected to another component such as a recharger.

FIG. 10 shows an alternative embodiment of the first, second, third, fourth, fifth, or sixth aspects of the invention to the sorbent cartridge shown in FIG. 9, wherein a first connector 71 and a flow valve 73 bypass flow through the second module 62 to a component 75. The component 75 can be a recharger used to recharge or clean the second module 62 while attached to the sorbent cartridge. In any embodiment of the first, second, third, fourth, fifth, or sixth aspects of the invention, the component 75 can be a container storing a fluid such as a wash fluid or recharging fluid. In any embodiment, of the first, second, third, fourth, fifth, or sixth aspects of the invention, the component 75 can be pump for pumping fluid. Upon passing through the component 75, fluid can return through the second connector 72 via the second valve 74, and into the third module 63. In any embodiment of the first, second, third, fourth, fifth, or sixth aspects of the invention, the component 75 can be removed after a period of time and fluid allowed to flow the third module 63 through the bypass first connector 72 and a flow valve 74. The component 75 can be reversibly attached and detached as necessary.

Figure 11:
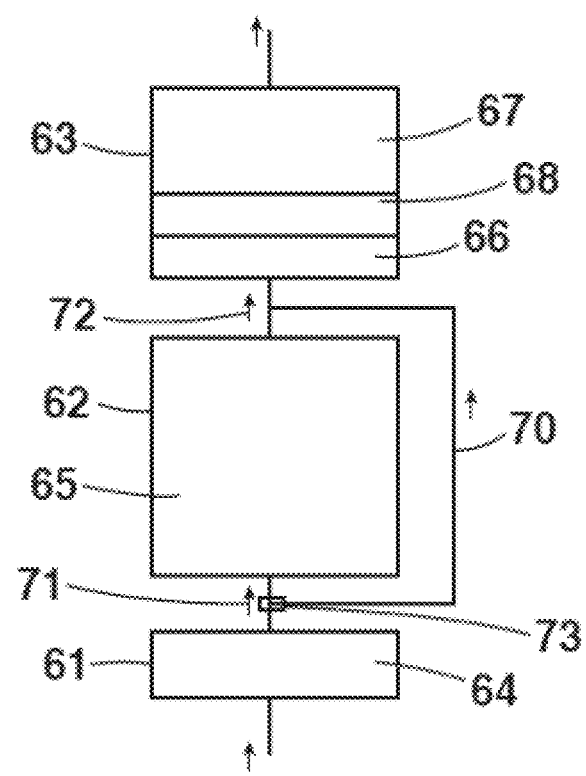
FIG. 11 shows a modular sorbent cartridge with three modules and an optional bypass line to direct fluid from the first to the third modules.

In an alternative to the embodiments shown in FIGS. 9 and 10, the bypass feature can be accomplished with a single three-way valve in the first, second, third, fourth, fifth, or sixth aspects of the invention, as shown in FIG. 11. Valve 73, positioned on the first connector 71, can direct fluid from the first module 61 to either the second module 62 or bypass line 70. In any embodiment of the first, second, third, fourth, fifth, or sixth aspects of the invention, a component may be added to bypass line 70, such as a recharger. In any embodiment of the first, second, third, fourth, fifth, or sixth aspects of the invention, the single valve may be positioned after the second module 62, on the second connector 72.

Figure 12:
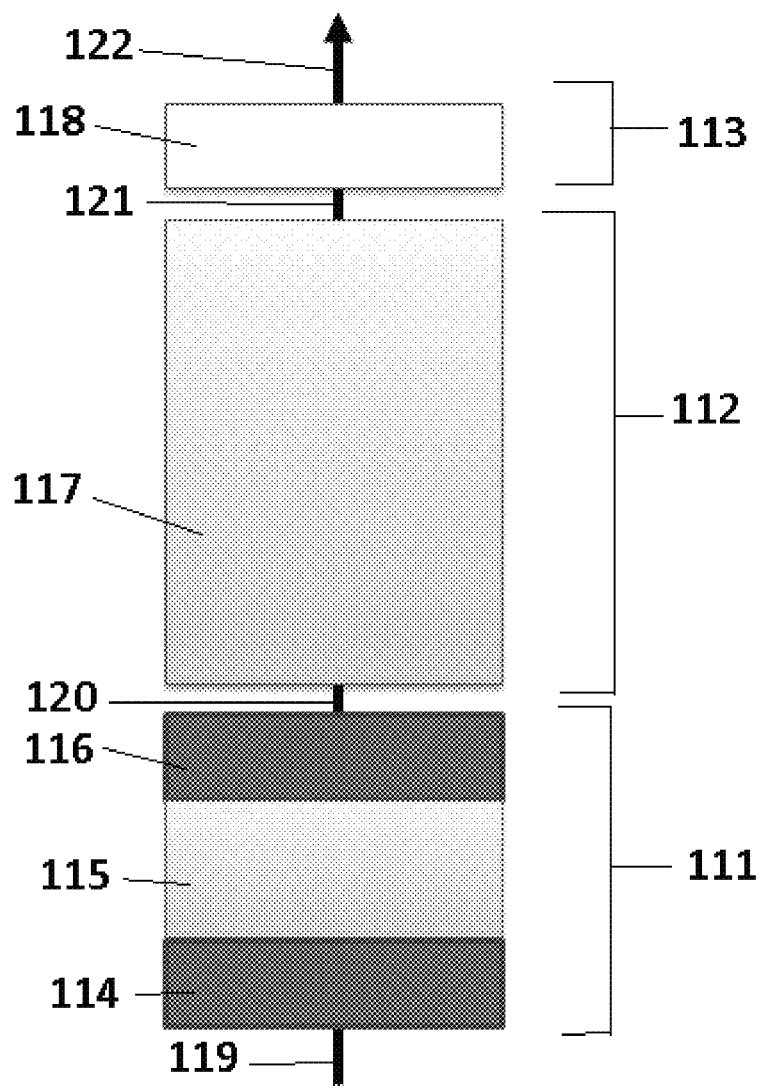
FIG. 12 shows a three module sorbent cartridge with activated carbon, alumina and urease in the first module, zirconium phosphate in the second module and zirconium oxide in the third module.

FIG. 12 shows a modular sorbent cartridge in accordance with the first, second, third, fourth, fifth, or sixth aspects of the invention. The sorbent cartridge in FIG. 12 comprises three modules 111, 112, and 113. Spent dialysate can enter the first module 111 through inlet 119. First module 111 can be configured to contain a layer of activated carbon 114 to remove nonionic toxins from the fluid by adsorption. After passing through activated carbon layer 114, the spent dialysate can pass into alumina and urease layer 115. Urease can catalyze the reaction of urea to form ammonia and carbon dioxide. The result of this is the formation of ammonium carbonate. The alumina serves as a support for the urease enzyme. After passing through the alumina and urease layer 115, the spent dialysate can pass through a second activated carbon layer 116. This second activated carbon layer 116 serves to adsorb any urease that may leach off of the alumina in urease and alumina layer 115. The activated carbon layer 114 can remove residual sterilants like citric acid, formaldehyde, peracetic acid and bleach left over from a hemodialysis session, disinfection, or dialyzer reprocessing. These residuals could damage the urease and alumina layer 115 if not removed first. The second activated carbon layer 116 can serve as a backup layer to retain urease that migrates beyond the urease and alumina layer 115. The second activated carbon layer 116 prevents migration of urease beyond the first module 111. Both the activated carbon layer 114 and the second activated carbon layer 116 can also remove uremic solutes like creatinine, uric acid, beta-2-macroglobulin and others. By adsorbing the urease onto activated carbon layer 116, the urease is prevented from migrating into the second module 112. The first module 111 can be a single use and optionally discarded after use without being recharged. This is particularly useful to separate expensive sorbent materials such as a zirconium phosphate and zirconium oxide from less expensive materials such as urease, alumina, and activated carbon.

After passing through the second activated carbon layer 116, the spent dialysate can pass out of the first module 111 through connector 120 and into the second module 112. The second module 112 can contain a cation exchanger 117 such as zirconium phosphate, which removes ammonium, calcium, potassium and magnesium cations and exchanges these cations for sodium and hydrogen cations. The second module 112 can be multi-use and detachable from the other modules to facilitate separate recharging.

After passing through the second module 112, the spent dialysate can flow through connector 121 and into the third module 113. Similar to the second module 112, the third module 113 can also be multi-use and detachable from other modules. The third module 113 can be configured to contain an anion exchanger such as zirconium oxide 118. The zirconium oxide layer 118 can remove phosphate and fluoride anions, exchanging these anions for acetate or hydroxide anions. The spent dialysate can then exit the third module 113 through outlet 122 and leave the sorbent cartridge.

Critically, by isolating the zirconium phosphate 117 in a separate module 112, recharging of the zirconium phosphate is facilitated. Similarly, by isolating the zirconium oxide 118 in a separate module 113, recharging of the zirconium oxide 118 is facilitated because zirconium oxide requires a base such as sodium hydroxide for recharging. The high pH necessary for recharging of the zirconium oxide may damage the zirconium phosphate, and thus cause excessive release of phosphate into the dialysate. In other words, separating zirconium oxide from zirconium phosphate can facilitate recharging of both materials. The zirconium phosphate is recharged with acidic solution, while the zirconium oxide is recharged with a basic solution. Extremes of high and low pH would also be deleterious to any urease layer during recharging. Thus, recharging each of the sorbent materials when the sorbents materials are isolated from each is thus beneficial to preserving the integrity of the other sorbent materials.

The first module 111 in FIG. 12 contains only activated carbon 114 and 116 and alumina and urease 115. These materials are less expensive than the zirconium oxide and zirconium phosphate contained in the other modules. As such, the first module 111 may be a single use module, with the module disposed of after each dialysis session. In any embodiment of the invention, the modules containing the more expensive sorbent materials zirconium oxide and zirconium phosphate can be multi-use modules, wherein after recharging of the modules, the modules can be reused.

As explained, phosphate anions may leach out from the zirconium phosphate sorbent material during use. Depending on the zirconium phosphate material used, anywhere between 100 mg/kg and 4,000 mg/kg or more of phosphate may leach from the zirconium phosphate sorbent material. Leaching of phosphate from the zirconium phosphate sorbent material could reduce the efficiency of phosphate removal from the patient, or even increase the phosphate level of the patient. By placing the zirconium oxide module downstream of the zirconium phosphate module, the phosphate that leaches from the zirconium phosphate can be recaptured by the zirconium oxide. Further, zirconium oxide can act as an anion exchange material at low pH, but a cation exchange material at high pH. As such, the capacity of the zirconium oxide to remove phosphate and other anions from the dialysate may be increased at the lower pH of the dialysate after passing through the zirconium phosphate layer.

One skilled in the art will understand that the second activated carbon layer may be eliminated. Further, in any embodiment of the first, second, third, fourth, fifth, or sixth aspects of the invention, the second activated carbon layer may be replaced by additional alumina to prevent urease migration.

Figure 13:
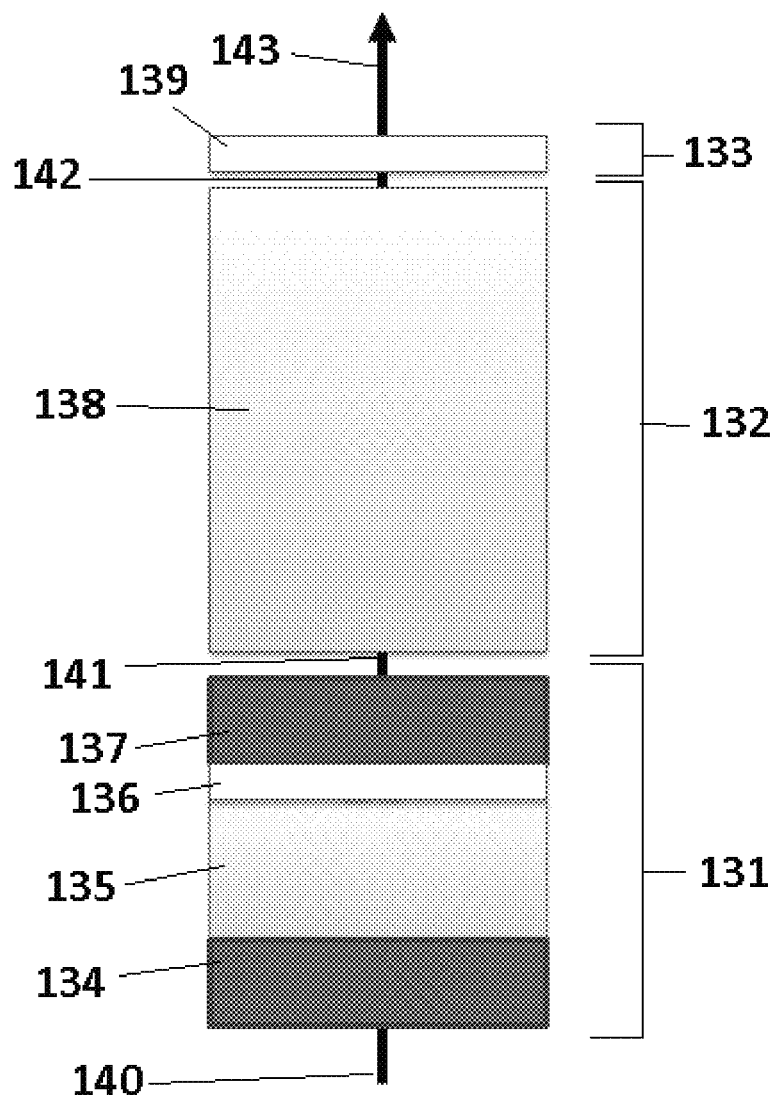
FIG. 13 shows a three module sorbent cartridge with activated carbon, alumina, urease and zirconium oxide in the first module, zirconium phosphate in the second module, and zirconium oxide in the third module.

FIG. 13 shows a sorbent cartridge in accordance with the invention having two zirconium oxide layers. A first module 131 can contain a first activated carbon layer 134, a layer of alumina and urease 135, a layer of zirconium oxide 136, and a second layer of activated carbon 137. A second module 132 can contain zirconium phosphate 138. A third module 133 can contain a second layer of zirconium oxide 139. As before, the second module 132 and third module 133 can be multi-use and detachable from the other modules to facilitate recharging.

Dialysate can enter the first module 131 through inlet 140. In the first module, non-ionic toxins can be removed by activated carbon 134, urea can be broken down into ammonium ions and carbon dioxide by urease and alumina 135, and phosphate and other anions can be removed by zirconium oxide layer 136. Second activated carbon layer 137 can serve to prevent urease migration out of the first module 131 and to remove any other non-ionic toxins still present in the dialysate. As explained, the second activated carbon layer 137 can be eliminated in any embodiment of the first, second, third, fourth, fifth, or sixth aspects of the invention, or replaced with additional alumina to prevent urease migration. The dialysate can then pass through connector 141 to second module 132 where calcium, magnesium, potassium and ammonium ions can be removed by the zirconium phosphate 138. The dialysate can then pass through connector 142 into third module 133, where any phosphate ions that leached out of zirconium phosphate 138 can be recaptured by zirconium oxide 139. Because some or all of the phosphate anions present in the dialysate initially will have been removed by zirconium oxide layer 136, less zirconium oxide may be necessary in the third module 133 in order to recapture the leached phosphate. In any embodiment of the first, second, third, fourth, fifth or sixth aspects of the invention, the amount of zirconium oxide in the first module 131 can be the same, more or less than the amount of zirconium oxide in the third module 133. After passing through the third module 133, the fluid can pass out of the sorbent cartridge through outlet 143.

In FIG. 13, second module 132 and third module 133 can be multi-use modules. These modules can be reused after recharging of the zirconium phosphate 138 and zirconium oxide 139 contained therein. The first module 131, containing activated carbon 134 and 137, alumina and urease 135, and zirconium oxide 136 can be single use, and disposable after completion of the dialysis session.

In any embodiment of the first, second, third, fourth, fifth, or sixth aspects of the invention, the order of the zirconium oxide 136 and alumina and urease 135 can be switched. That is, the zirconium oxide 136 can be placed in the first module 131 upstream of the alumina and urease 135. In any embodiment of the first, second, third, fourth, fifth, or sixth aspects of the invention, the alumina and urease 135 can be intermixed with the zirconium oxide 136 as opposed to being arranged in separate layers as shown in FIG. 13.

In any embodiment of the first, second, third, fourth, fifth, or sixth aspects of the invention, the sorbent cartridge may only have a single activated carbon layer. Placing the activated carbon layer upstream of the urease layer may be beneficial in order to ensure removal of residual sterilants such as citric acid, formaldehyde, peracetic acid and bleach left over in the dialysis system from disinfection or dialyzer reprocessing. In any embodiment of the first, second, third, fourth, fifth, or sixth aspects of the invention, the second downstream activated carbon layer can also be included, as shown in FIG. 12, in order to prevent urease migration as described herein.

In any embodiment of the first, second, third, fourth, fifth, or sixth aspects of the invention, a multi-use module, such as modules 132 and 133 of FIG. 13, can be detached from the other modules present for recharging. The user can disconnect the multi-use module from the other modules in the sorbent cartridge, and pass a recharging solution through the multi-use module. A module containing zirconium phosphate can be recharged by passing fluid containing sodium ions and acid. This recharging process can be done sequentially, such as by first passing a sodium solution through the module and then passing an acidic solution through the module, or the recharging can be done with a single acidic solution that also contains sodium ions.

A module containing zirconium oxide can be recharged by passing a solution comprising sodium hydroxide or other basic aqueous solution through the module. In any embodiment of the first, second, third, fourth, fifth, or sixth aspects of the invention, the recharging solution can be a solution of lithium hydroxide, potassium hydroxide or any other basic aqueous solution. The high pH of the solution used to recharge the zirconium oxide may damage the zirconium phosphate. Separating the zirconium phosphate and zirconium oxide into separate modules therefore allows both sorbent materials to be recharged.

The modules, once recharged, can be reconnected to each other, and to a new single use module for a new dialysis session. In any embodiment of the first, second, third, fourth, fifth, or sixth aspects of the invention, the single-use and multi-use modules can be designed to ensure the proper order of modules in the assembled sorbent cartridge. As explained, including the zirconium oxide containing module downstream of the zirconium phosphate containing module allows recapture of any phosphate anions that leach off of the zirconium phosphate. Further, a zirconium phosphate containing module must be at least downstream of the urease containing module so that the zirconium phosphate can adsorb the ammonium ions created by the breakdown of urea by the urease. In any embodiment of the first, second, third, fourth, fifth or sixth aspects of the invention, zirconium phosphate can also be present in a module upstream of the urease, as explained. The connections described herein can be different on the topsides and bottom sides of each module to ensure the proper order. For example, the connector on the bottom side of the zirconium phosphate module may be configured to cooperatively engage with a connector on the top side of the single use module. At the same time, the connector on the bottom side of the zirconium phosphate module can be configured so that the zirconium phosphate module will not cooperatively engage with the connector on the top side of the zirconium oxide module. This will ensure that the user cannot place the zirconium oxide module upstream of the zirconium phosphate module. In any embodiment of the first, second, third, fourth, fifth, or sixth aspects of the invention, the modules can be color coded or marked in any other fashion to alert the user to the proper order of modules in the assembled sorbent cartridge.

Figure 14:
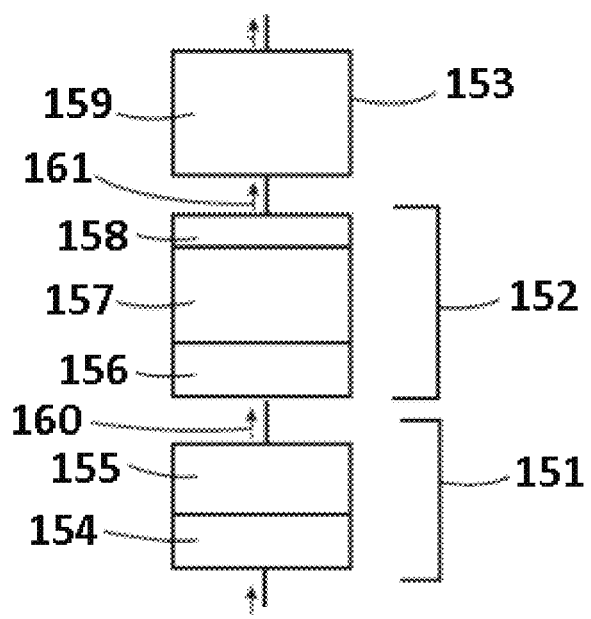
FIG. 14 shows a three module sorbent cartridge with activated carbon, alumina and urease in the first module, alumina, activated carbon and zirconium phosphate in the second module, and zirconium oxide in the third module.

In any embodiment of the first, second, third, fourth, fifth, or sixth aspects of the invention, as shown in FIG. 14, alumina, urease and activated carbon can be present in the same module as the zirconium phosphate. Fluid entering the sorbent cartridge shown in FIG. 14 can enter a first module 151. The first module 151 can contain activated carbon 154 and alumina and urease 155. The activated carbon 154 can remove non-ionic toxins, while the urease in the alumina and urease layer 155 can catalyze the breakdown of urea into ammonium ions and carbon dioxide. After passing through the first module 151, the fluid can enter the second module 152 through connector 160. The second module can contain alumina layer 156, activated carbon layer 157 and zirconium phosphate 158. The alumina 156 can serve to capture any urease that has migrated off of the alumina in urease and alumina layer 155. The second activated carbon layer 157 can serve to remove any remaining non-ionic toxins and protect the zirconium phosphate layer 158. The zirconium phosphate layer 158 can remove potassium, calcium, magnesium, ammonium and other cations, exchanging these cations for sodium and hydrogen ions. After passing through the second module 152, the fluid can enter the third module 153 through connector 161. The third module 153 can contain zirconium oxide 159. The zirconium oxide 159 can remove any potassium, fluoride or other anions, including phosphate that has leached out of the zirconium phosphate layer 158, exchanging these anions for acetate or hydroxide anions.

Including activated carbon and alumina in the same module as zirconium phosphate may not impede the recharging of the zirconium phosphate. As explained, zirconium phosphate can be recharged by passing an acidic solution containing sodium cations through the zirconium phosphate. In any embodiment of the first, second, third, fourth, fifth, or sixth aspects of the invention, this recharging solution can be heated. A heated solution of low pH will be capable of removing urease from alumina. Further, a heated solution can also remove the waste species that have been attached to the activated carbon. As such, the same solution or solutions that can be used to recharge zirconium phosphate can be used to recharge the alumina and activated carbon.

Figure 15:
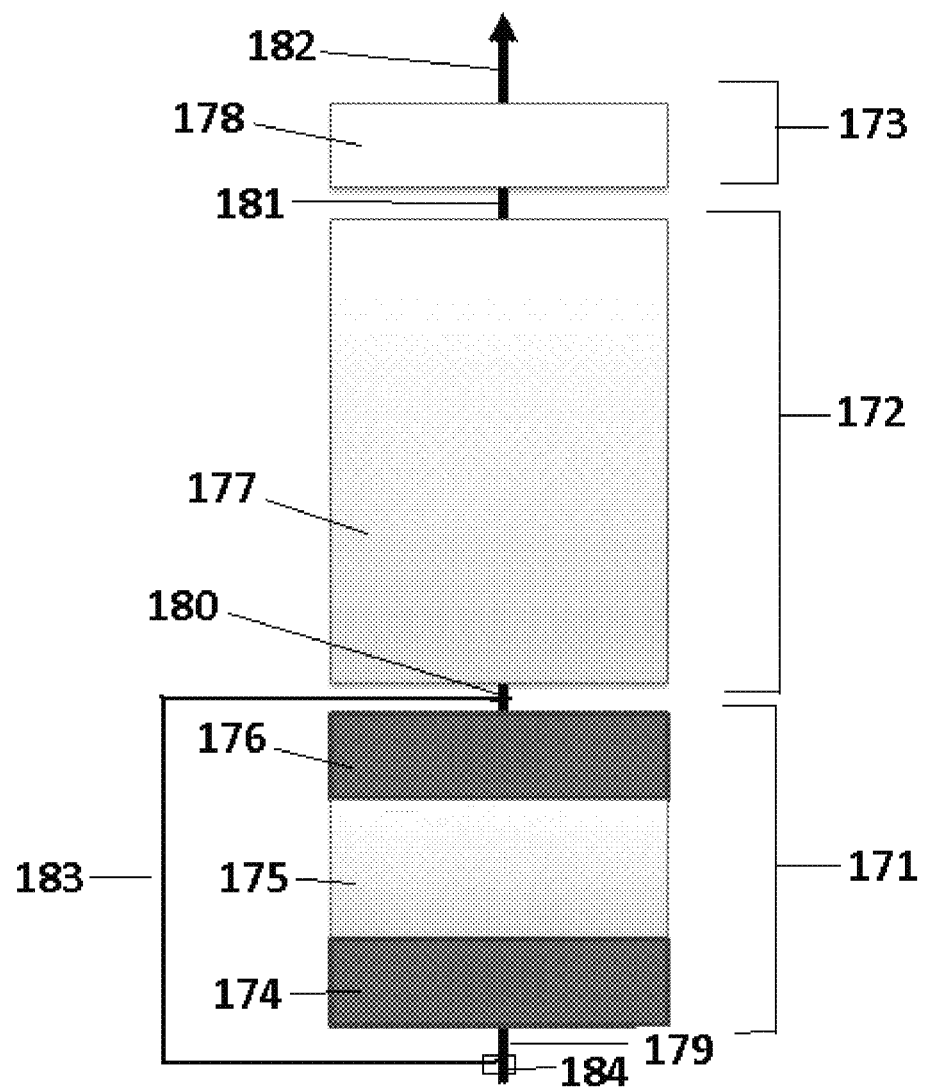
FIG. 15 shows a three-module sorbent cartridge with a bypass line and valve to allow for bypass of a urease containing first module.

In any embodiment of the first, second, third, fourth, fifth, or sixth aspects of the invention, the sorbent cartridge can include one or more bypass lines, allowing fluid to bypass one or more of the sorbent modules, as illustrated in FIG. 15. FIG. 15 illustrates a three-module sorbent cartridge including a bypass line 183 that allows for bypass of a urease containing module 171 in the event of ammonia breakthrough. Ammonia breakthrough can occur when the capacity of the zirconium phosphate layer to exchange ammonium ion is exceeded. In the event of ammonia breakthrough, the spent dialysate can bypass the first module 171, which contains the activated carbon layer 174, alumina and urease layer 175 and a second activated carbon layer 176. Valve 184 on first connector 179 can control the movement of fluid into the bypass line 183, bypassing the entire first module 171. By bypassing the urease containing layer 175, the breakdown of urea into ammonium ions is prevented. In normal operation, the valve 184 can be set to allow the fluid to pass into the first module 171 and only switched to bypass line 183 in the event of ammonia breakthrough. After passing through the first module 171 fluid can enter the second module 172 through second connector 180. The second module can contain zirconium phosphate 177, which would normally remove ammonium ions from the fluid. The bypass line 183 can allow fluid to enter the second module 172 as illustrated in FIG. 15, or to also bypass the second module 172 and connect back to the main operational line of the sorbent cartridge before third module 173. The fluid then passes through the second connector 181, and into the third module 173. The third module can contain a zirconium oxide layer 178. After passing through the third module, a regenerated dialysate can exit the sorbent cartridge through connector 182. In the event of ammonia breakthrough, the valve 184 can be set to redirect the fluid into bypass line 183. This line will cause the fluid not to enter the first module 171, and therefore the urea will not be broken down into ammonia in the alumina/urease layer. The fluid will instead be directed to the second connector 180, and then the third module 173. In this way dialysis may continue, while avoiding the creation of ammonia. The valve assembly can also include an access point for a sensor. The access point can be a portion of the valve assembly wherein a sensor can contact the fluid to take measurement data such as a flow or pressure reading. The form and construction of such access points contemplated by the present invention are those known to one of ordinary skill in the art.

In any embodiment of the first, second, third, fourth, fifth, or sixth aspects of the invention utilizing a bypass line, a further layer of activated carbon can be included in an additional module. This will allow non-ionic toxins to continue to be removed, even after ammonium breakthrough occurs.

To make use of the modular sorbent cartridge easier, the valve assembly in any embodiment of the first, second, third, fourth, fifth, or sixth aspects of the invention may be operated by a programmable controller or computer system that can be programmed to regulate flow through the valves and into and out of the modules. An optical sensor, photocell or other flow sensing apparatus may detect the flow of fluid through any two points in the sorbent cartridge. For example, an optical fluid flow device can be provided for measuring flow wherein the device includes an optical fluid pressure measuring device having sensors positioned in any one of the flow paths between the modules, in the connectors, or in the valve assemblies. Preferably, the sensors will be placed in a passageway defined between the modules. In any embodiment of the first, second, third, fourth, fifth, or sixth aspects of the invention, the optical fluid sensors can be connected to an interferometer associated with an opto-electronic demodulator which has an output signal representing the differential pressure between the two sensed areas. In any embodiment of the first, second, third, fourth, fifth, or sixth aspects of the invention, a flow sensing apparatus can have a flow-responsive element projecting into a fluid flow path, and a position sensor associated with the element which detects a change in position of the flow responsive element in response to the fluid flow. The flow-responsive element can be made of a wide variety of materials having the desired properties known to those of ordinary skill in art.

It will be apparent to one skilled in the art that various combinations and/or modifications and variations can be made in the dialysis system depending upon the specific needs for operation. Features illustrated or described as being part of one aspect of the invention may be used in the aspect of the invention, either alone or in combination.

We claim:

1. A sorbent cartridge, comprising:
a first module configured to contain urease;
a second module fluidly connectable to the first module and downstream of the first module, the second module configured to contain a cation exchanger; and
a third module fluidly connectable to the second module and downstream of the second module, the third module configure to contain an anion exchanger; and
wherein at least one module is a rechargeable module; wherein the rechargeable module is reversibly attachable and detachable to a recharger.

2. The sorbent cartridge of claim 1, wherein the cation exchanger is zirconium phosphate contained in the second module and the anion exchanger is zirconium oxide contained in the third module.

3. The sorbent cartridge of claim 1, wherein the first module is single-use, the second module is multi-use, and the third module is multi-use.

4. The sorbent cartridge of claim 1, wherein the first module contains any one of activated carbon, ion exchange resin, alumina, urease, and combinations and mixtures thereof.

5. The sorbent cartridge of claim 1, wherein the first module has a first layer of activated carbon, a second layer of alumina and urease downstream of the first layer, and a third layer of activated carbon downstream of the second layer.

6. The sorbent cartridge of claim 5, wherein a layer of zirconium oxide is positioned downstream of the second layer and upstream of the third layer.

7. The sorbent cartridge of claim 1, wherein the first module is fluidly connectable to a dialysate flow path upstream of the first module, and the third module is fluidly connectable to a dialysate flow path downstream of the third module.

8. The sorbent cartridge of claim 2, wherein the zirconium oxide is present both upstream and downstream of the zirconium phosphate.

9. The sorbent cartridge of claim 8, wherein an amount of the zirconium oxide upstream of the zirconium phosphate is less than an amount of the zirconium oxide downstream of the zirconium phosphate.

10. The sorbent cartridge of claim 1, wherein the second module comprising the cation exchanger is multi-use, and the third module comprising the anion exchanger is multi-use.

11. The sorbent cartridge of claim 2, the second module having the proviso that zirconium oxide and zirconium phosphate are not contained together in the same module.

12. The sorbent cartridge of claim 2, wherein the second module does not comprise any other sorbent materials other than zirconium phosphate.

13. The sorbent cartridge of claim 1, further comprising a bypass flow path fluidly connecting a position upstream of the first module to the second module.

14. The sorbent cartridge of claim 1, wherein the first module has a first layer of activated carbon, and a second layer of alumina and urease downstream of the first layer, and the second module has a first layer of alumina, a second layer of activated carbon downstream of the first layer, and a third layer of zirconium phosphate downstream of the second layer.

15. A sorbent cartridge, comprising:
at least one module configured to contain a cation exchanger; and
at least one module configured to contain an anion exchanger, wherein the module configured to contain the anion exchanger is fluidly connectable to and downstream of the module configured to contain a cation exchanger; and
wherein at least one module is a rechargeable module; wherein the rechargeable module is reversibly attachable and detachable to a recharger.

16. The sorbent cartridge of claim 15, wherein the cation exchanger is zirconium phosphate and the anion exchanger is zirconium oxide.

17. The sorbent cartridge of claim 15, wherein the module configured to contain the cation exchanger and the module configured to contain the anion exchanger are multi-use.

18. The sorbent cartridge of claim 15, wherein the module configured to contain the cation exchanger and the module configured to contain the anion exchanger are detachable.

19. The sorbent cartridge of claim 16, further comprising at least a second module upstream of the module configured to contain zirconium phosphate, the second module configured to contain any one of activated carbon, alumina, urease, and combinations thereof.

20. The sorbent cartridge of claim 19, wherein the second module further comprises zirconium oxide.

21. The sorbent cartridge of claim 20, wherein an amount of the zirconium oxide within the second module is less than an amount of the zirconium oxide downstream of the zirconium phosphate.

22. The sorbent cartridge of claim 1, wherein the anion exchanger is a material that can bind a molecule having a negative charge and exchange another molecule having a negative charge for the bound molecule.

23. The sorbent cartridge of claim 1, wherein the cation exchanger is a material that can bind a molecule having a positive charge and exchange another molecule having a positive charge for the bound molecule.

* * * * *